(12) United States Patent
Takagi et al.

(10) Patent No.: US 9,901,490 B2
(45) Date of Patent: Feb. 27, 2018

(54) DISPOSABLE PANT TYPE UNDERGARMENT AND METHOD FOR MANUFACTURING THE SAME

(71) Applicant: KOYO CORPORATION, Kanagawa (JP)

(72) Inventors: Takamasa Takagi, Kanagawa (JP); Takehisa Mitsugi, Kanagawa (JP); Munetada Matsumiya, Kanagawa (JP); Kazuya Ise, Kanagawa (JP); Satoshi Katayama, Kanagawa (JP)

(73) Assignee: KOYO CORPORATION, Kanagawa (JP)

( * ) Notice: Subject to any disclaimer, the term of this patent is extended or adjusted under 35 U.S.C. 154(b) by 0 days.

(21) Appl. No.: 14/984,971

(22) Filed: Dec. 30, 2015

(65) Prior Publication Data

US 2016/0113824 A1    Apr. 28, 2016

Related U.S. Application Data

(63) Continuation of application No. PCT/JP2015/050854, filed on Jan. 14, 2015.

(30) Foreign Application Priority Data

Jan. 14, 2014 (JP) ................................ 2014-004232

(51) Int. Cl.
*A61F 13/20* (2006.01)
*A61F 13/49* (2006.01)
(Continued)

(52) U.S. Cl.
CPC .. *A61F 13/49011* (2013.01); *A61F 13/15804* (2013.01); *A61F 13/49017* (2013.01);
(Continued)

(58) Field of Classification Search
CPC .......... A61F 13/49011; A61F 13/15804; A61F 13/49019; A61F 2013/49041; A41B 9/001; A41B 2400/52
(Continued)

(56) References Cited

U.S. PATENT DOCUMENTS

2002/0129888 A1    9/2002   Otsubo et al.
2005/0010188 A1    1/2005   Glaug et al.
(Continued)

FOREIGN PATENT DOCUMENTS

EP        1 249 214 A2    10/2002
JP        2002-272781 A    9/2002
(Continued)

OTHER PUBLICATIONS

International Search Report issued in Application No. PCT/JP2015/050854, dated Apr. 28, 2015.
(Continued)

*Primary Examiner* — Tatyana Zalukaeva
*Assistant Examiner* — Andrew J Mensh
(74) *Attorney, Agent, or Firm* — Michael Best & Friedrich LLP

(57) ABSTRACT

A disposable pant type undergarment includes a ventral member, a dorsal member and a crotch member that bridges the ventral member and the dorsal member. A crotch edge of the ventral member and the dorsal member each includes right and left edge lines, right and left tilted lines and a central line. The edge lines are approximately parallel in a waist-around direction. Nearer the central line, a distance between a waist opening of the undergarment and the tilted lines of the ventral member is shorter, and a distance between the waist opening and the tilted lines of the dorsal member is longer. Tilted portions of a leg-surrounding elastic body extend in a leaving direction from the crotch edge of the ventral member and extend into an area overlapped with the ventral member and the crotch member.

6 Claims, 15 Drawing Sheets

(51) Int. Cl.
　　　*A61F 13/15*　　(2006.01)
　　　*A41B 9/00*　　(2006.01)

(52) U.S. Cl.
　　　CPC ........ *A61F 13/49019* (2013.01); *A41B 9/001* (2013.01); *A41B 2400/52* (2013.01); *A61F 2013/49041* (2013.01)

(58) Field of Classification Search
　　　USPC .................................................. 604/385.29
　　　See application file for complete search history.

(56) References Cited

U.S. PATENT DOCUMENTS

| | | | |
|---|---|---|---|
| 2010/0193111 A1 | 8/2010 | Wada et al. | |
| 2011/0288517 A1* | 11/2011 | Mori | A61F 13/15756 604/385.3 |
| 2012/0090779 A1* | 4/2012 | Nakamura | A61F 13/15609 156/324 |
| 2012/0095430 A1* | 4/2012 | Nakaoka | A61F 13/49017 604/385.25 |
| 2013/0226127 A1 | 8/2013 | Takahashi et al. | |

FOREIGN PATENT DOCUMENTS

| | | |
|---|---|---|
| JP | 2010-227654 A | 10/2010 |
| JP | 2011-212373 A | 10/2011 |
| JP | 2012-100857 A | 5/2012 |
| WO | WO-2005/007051 A1 | 1/2005 |

OTHER PUBLICATIONS

Extended Search Report issued in European Application No. 15737201.2, dated Sep. 28, 2017.

* cited by examiner

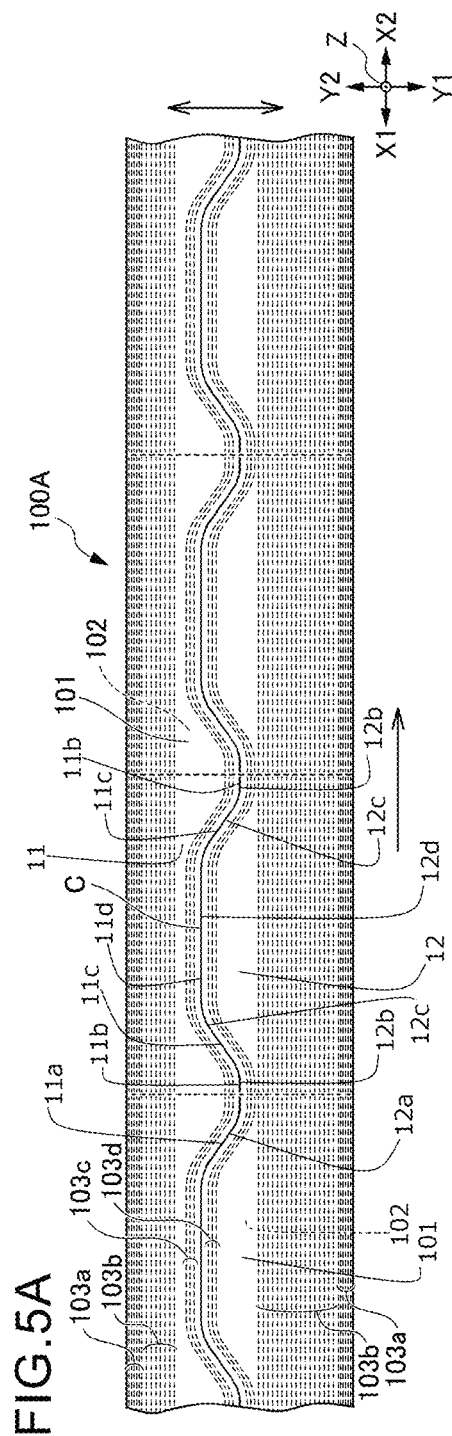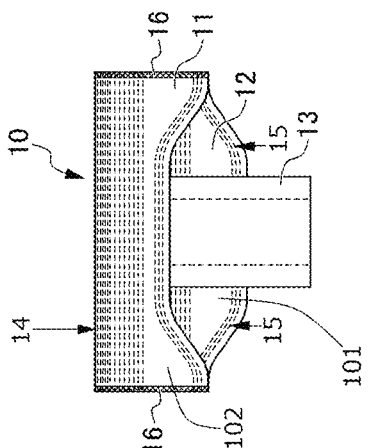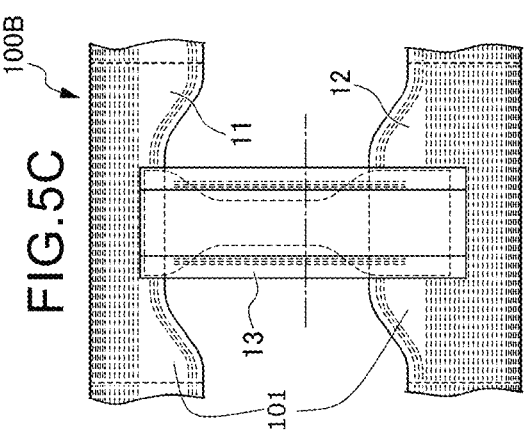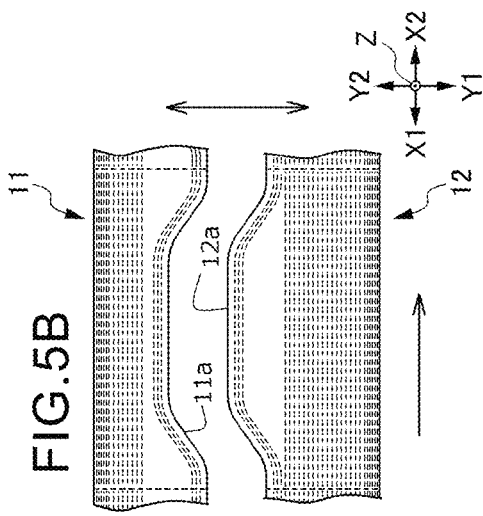

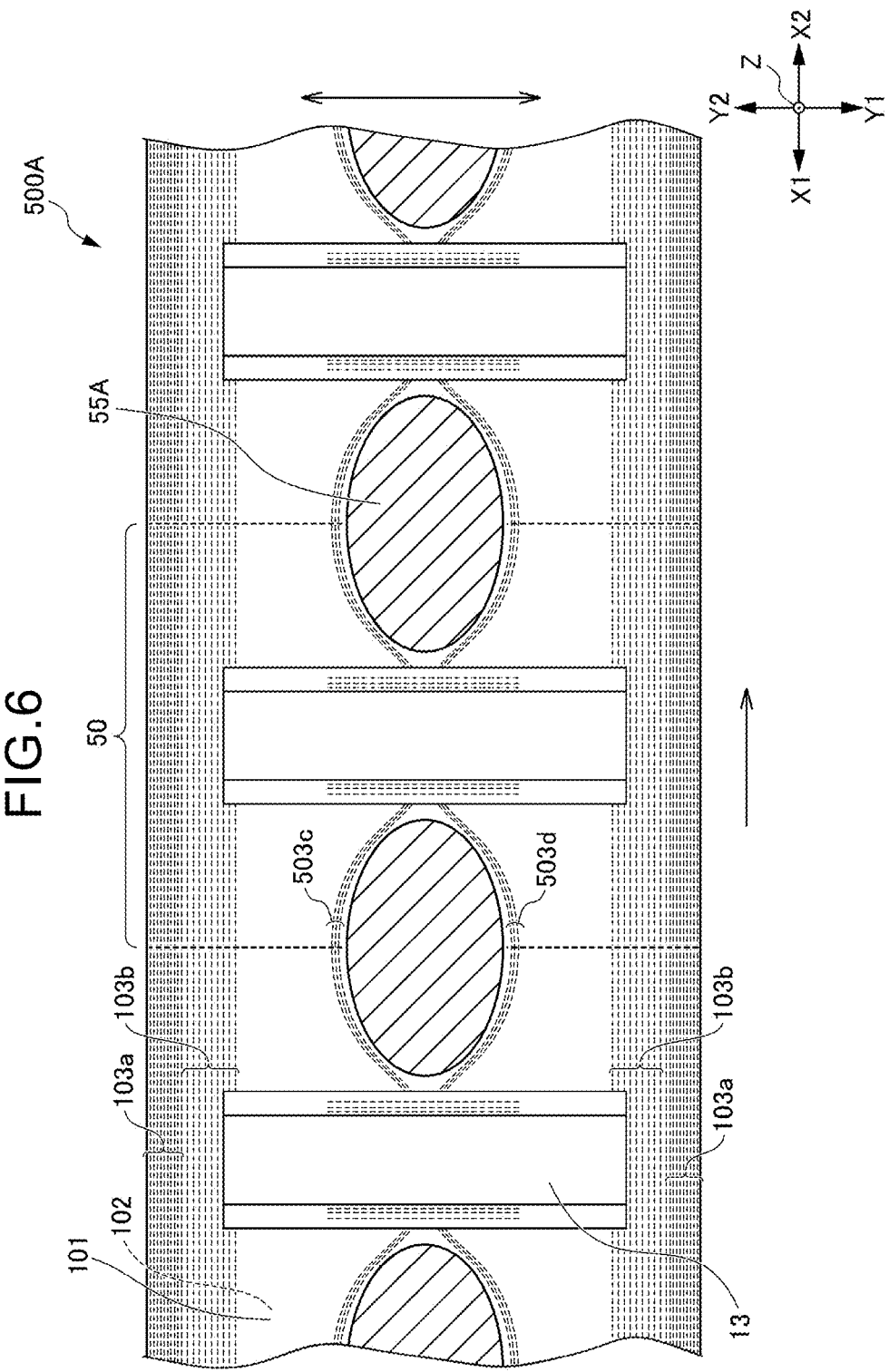

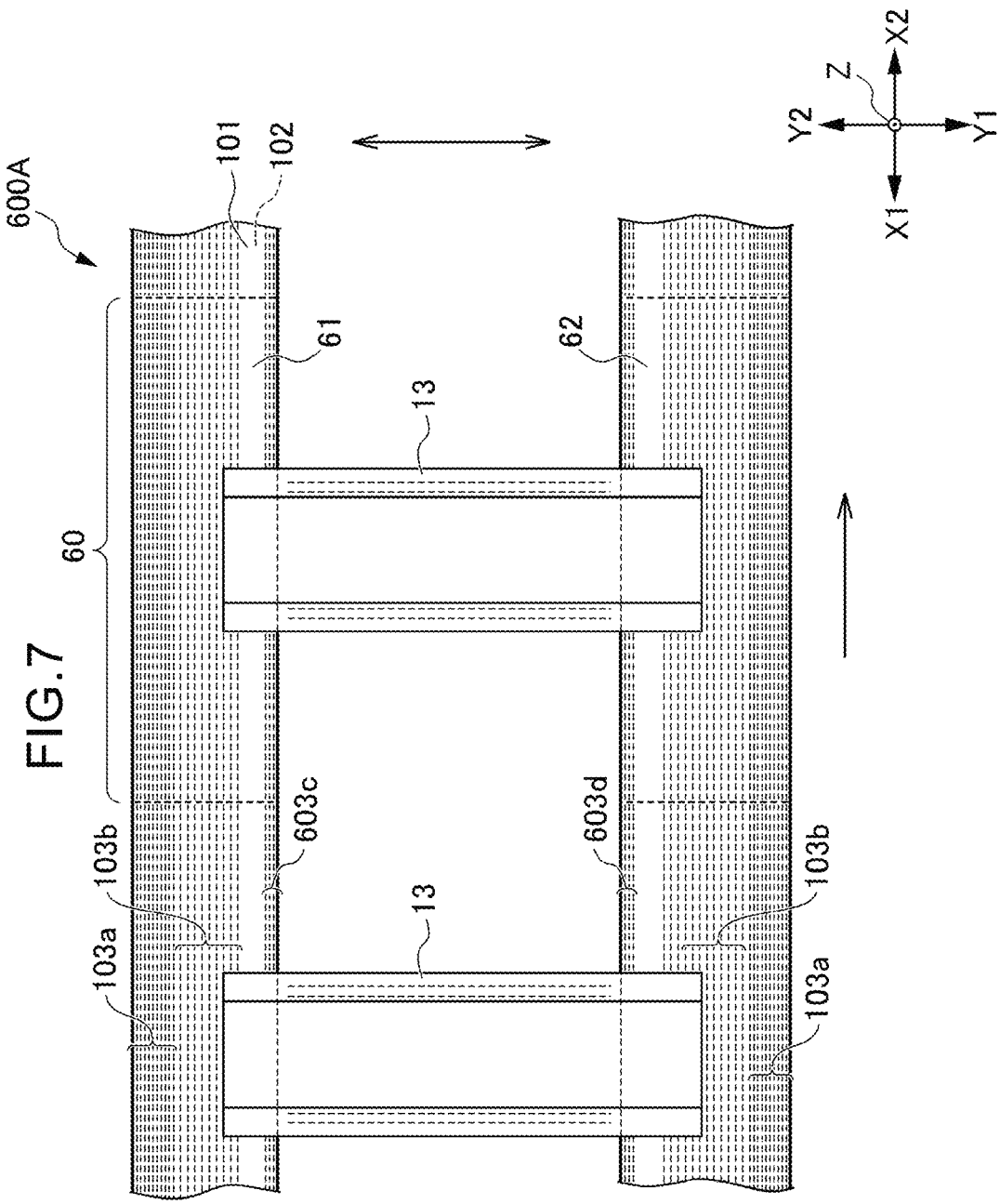

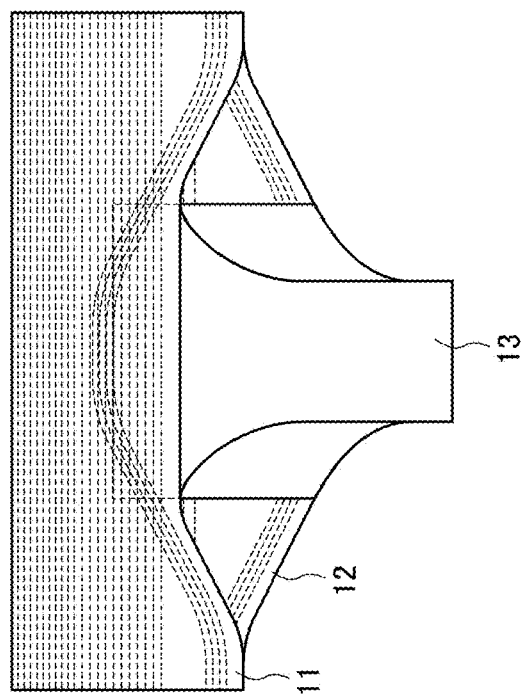
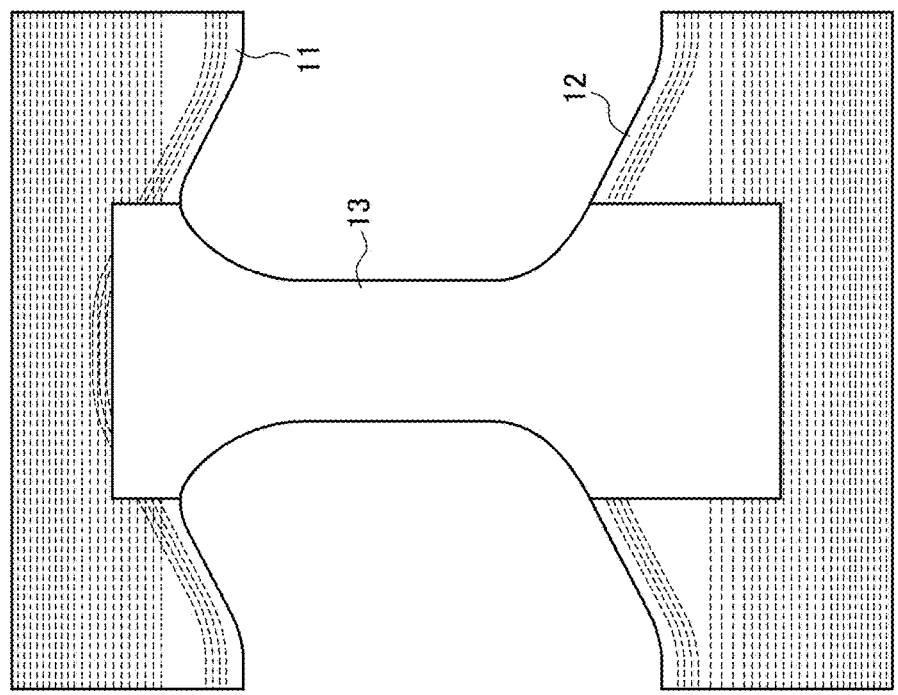

DISPOSABLE PANT TYPE UNDERGARMENT AND METHOD FOR MANUFACTURING THE SAME

CROSS-REFERENCES TO RELATED APPLICATION

This is a continuation of PCT/JP2015/050854 filed on Jan. 14, 2015, that claims priority from Japanese Patent Application No. 2014-004232 filed on Jan. 14, 2014. The contents of these two applications are incorporated herein by reference in their entirety.

TECHNICAL FIELD

The present invention relates to a disposable pant type undergarment such as a pant type diaper and a pant type pad-holder and a method for manufacturing the same.

BACKGROUND ART

A process for continuously manufacturing conventional pant type diapers and pad-holders forms through holes or cutouts for leg openings into which a wearer's legs are inserted, by trimming part of the strip-shaped whole cloth which constitutes an external body thereof. Besides, a pant type diaper and a pant type pad-holder which are formed by arranging a rectangular ventral member and a rectangular dorsal member so as to be connected by a crotch member have been known.

SUMMARY OF THE INVENTION

The invention of this application relates to a disposable pant type undergarment that includes a ventral member, a dorsal member and a crotch member. The crotch member bridges the ventral member and the dorsal member bonded at center portions of the ventral member and the dorsal member. A waist opening is surrounded by the ventral member and the dorsal member, wherein right and left side edges of the ventral member and right and left side edges of the dorsal member are bonded. Right and left leg openings are surrounded by the ventral member, the dorsal member and the crotch member. Waist elastic bodies are extended on the ventral member and the dorsal member in a waist-around direction. A first leg-surrounding elastic body is extended at least on the ventral member around the right and left leg openings. A second leg-surrounding elastic body extended at least on the dorsal member around the right and left leg openings.

A crotch edge of the ventral member includes right and left edge lines, right and left tilted lines and a central line. The edge lines are approximately parallel in the waist-around direction. The edge lines are connected to the tilted lines. The tilted lines are connected to the central line. A distance between the tilted lines and the waist opening is shorter, being nearer the central line. A crotch edge of the dorsal member includes right and left edge lines, right and left tilted lines and a central line. The edge lines are approximately parallel in the waist-around direction. The edge lines are connected to the tilted lines. The tilted lines are connected to the central line. A distance between the tilted lines and the waist opening is longer, being nearer the central line. The first leg-surrounding elastic body includes right and left edge lines, right and left tilted lines and a central line. The edge portions are extended along the edge lines of the ventral member. The edge portions are connected to the tilted portions. The tilted portions are connected to the central portion. The tilted portions extend in a leaving direction from the crotch edge of the ventral member and extend into an area overlapped with the ventral member and the crotch member.

The second leg-surrounding elastic body includes right and left edge lines, right and left tilted lines and a central line. The edge portions are extended along the edge lines of the dorsal member. The edge portions are connected to the tilted portions. The tilted portions are connected to the central portion. The tilted portions extend in an approaching direction to the crotch edge of the dorsal member.

A method of manufacturing the disposable pant type undergarment includes the steps of: forming a web-like layered body, wherein the layered body comprises an inner sheet and an outer sheet, the layered body further comprises the waist elastic bodies, the first leg-surrounding elastic body and the second leg-surrounding elastic body between the inner sheet and the outer sheet, the waist elastic bodies are extended in a web stream direction, the first elastic body and the second elastic body are extended periodically in a web stream direction; cutting the layered body along a cut plan line thereby dividing the layered body into a first continuous body that comprises the ventral member and a second continuous body that comprises the dorsal member, wherein the cut plan line includes the crotch edge of the ventral member that coincides the crotch edge of the dorsal member, the first leg-surrounding elastic body and the second leg-surrounding elastic body are arranged along the cut plan line; widening the distance between the first and second continuous bodies in a web-width direction; bonding the crotch member onto the ventral member and the dorsal member at the central portions of the ventral member and the dorsal member; folding the first and second continuous bodies at the crotch member so that the inner sheets of the first and second continuous bodies meet together; bonding the continuous bodies at a line perpendicular to the web stream direction in every periodicity; and cutting the bonded continuous bodies in every periodicity to form the pant type undergarments.

BRIEF DESCRIPTION OF THE DRAWINGS

FIGS. 5A-5D show steps of manufacturing the pant type diaper 10 of the first embodiment.

FIG. 6 is a drawing to explain the pant type diaper 50 of Comparative Example 1.

FIG. 7 is a drawing to explain the pant type diaper 60 of Comparative Example 2.

FIGS. 15A and 15B show the shape of the absorbing member 13 which is the crotch member of a modified embodiment.

DESCRIPTION OF THE INVENTION

By referring to the attached drawings, embodiments of the disposable pant type undergarment and the method for manufacturing the same in the present invention will be explained. Including FIG. 1, in order to help in understanding, each drawing shown below is a schematic drawing, so that the size and shape of each part are arbitrarily exaggerated.

Because the number in the size, the name, and a like of the material in each member described in the specification are mere examples as embodiments, they are not limited to those shown below; and therefore, they may be used by arbitrarily selecting them.

First Embodiment

As the first embodiment of the disposable pant type undergarment of the present invention, the pant type diaper 10 will be explained.

Figure 1:
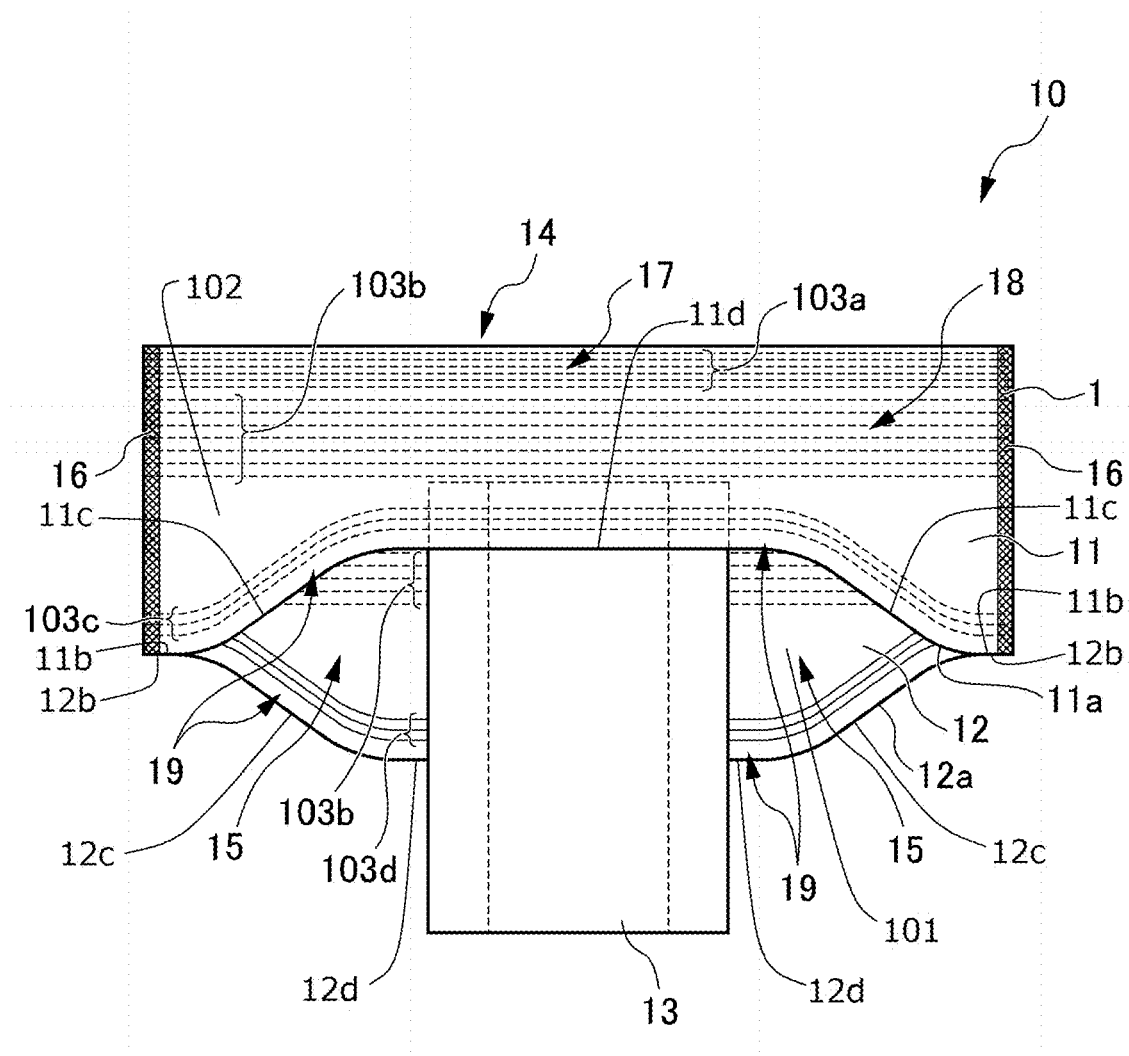
FIG. 1 shows the pant type diaper 10 of a first embodiment.
Figure 2:
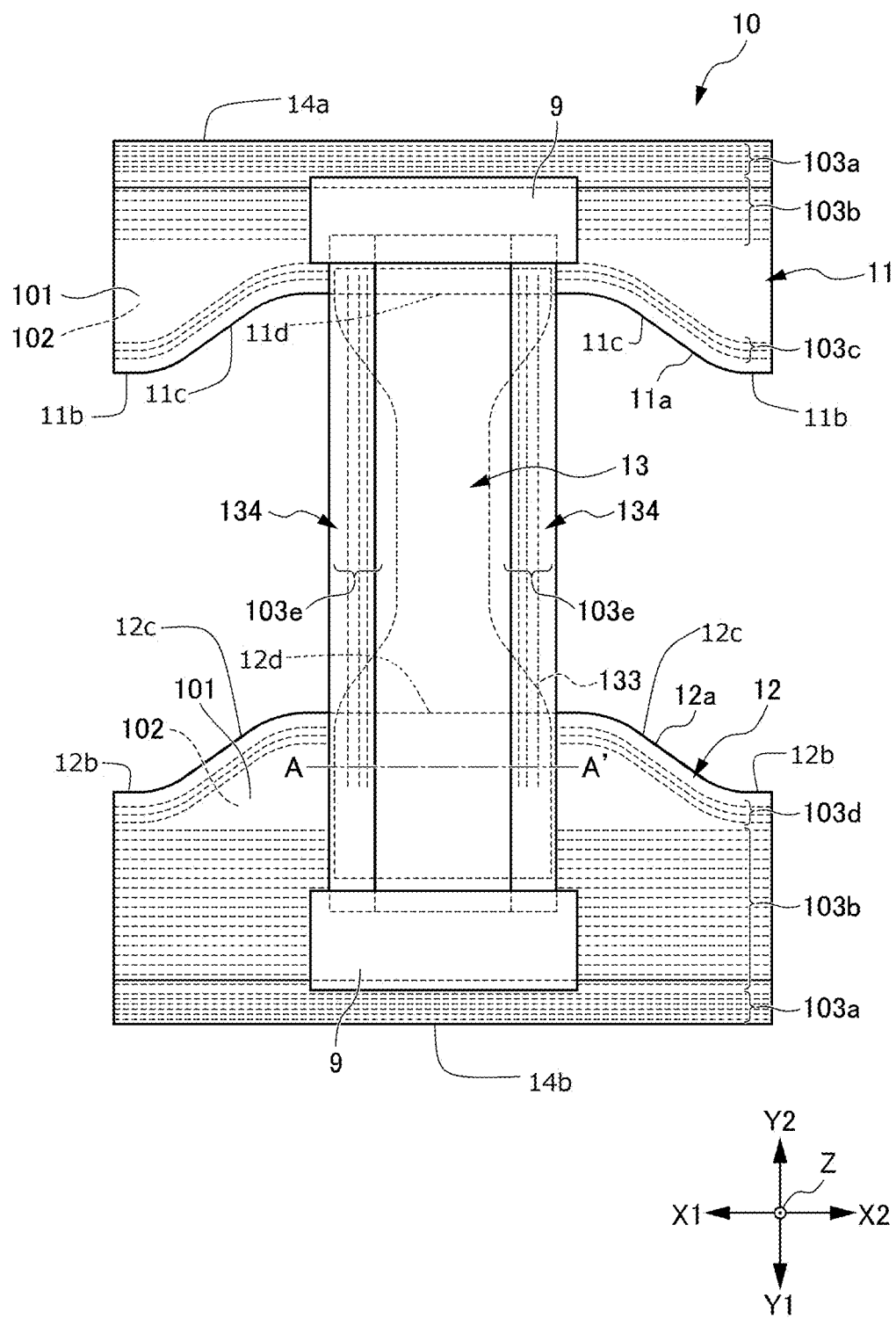
FIG. 2 shows the pant type diaper 10 of the first embodiment that is extended to a planar view.
Figure 3:
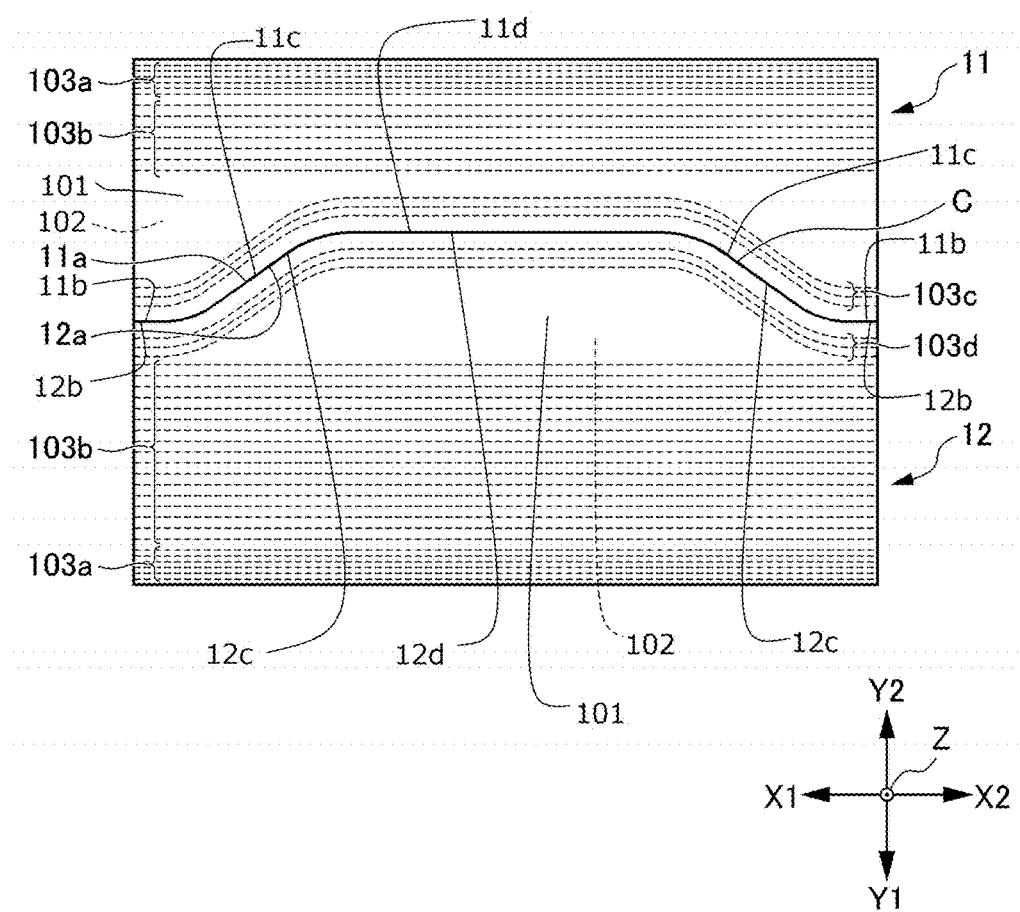
FIG. 3 is a drawing to explain the first leg-surrounding elastic body 103c, the second leg-surrounding elastic body 103d, and the cut plan line C of the pant type diaper 10 of the first embodiment.

FIG. 1 is a drawing to show the pant type diaper 10 of the first embodiment. FIG. 2 is a drawing to show the pant type diaper 10 of the first embodiment that is extended to a planar view. FIG. 3 is a drawing to explain the first leg-surrounding elastic body 103c, the second leg-surrounding elastic body 103d, and the cut plan line C of the pant type diaper 10 of the first embodiment.

In order to help in understanding, in FIG. 1 to FIG. 3 and each drawing shown thereafter, the elastic body 103 mentioned later is shown in the extended state (in the state of not expressing a shrinking force). Also, in FIG. 2 and each drawing shown thereafter, in order to help in understanding, in the extended pant type diaper, the XYZ coordinate is used when necessary, wherein the width direction (the waist-around direction of a wearer, i.e., the right-left direction of a wearer) is shown as the X-axis, the front-back direction is shown as the Y-axis, and the thickness direction is shown as the Z-axis. In this X-axis, the X1 side is the left side of a wearer and the X2 side is the right side of a wearer; in the Y-axis, the Y1 side is the back side (dorsal side) of a wearer and the Y2 side is the front side (ventral side) of a wearer; and in the Z-axis, the Z1 side is the outer side (cloth side of a wearer) and the Z2 side is the inner side (skin side of a wearer).

As shown in FIG. 1, the pant type diaper 10 comprises the ventral member 11 disposed on the wearer's ventral side upon putting it on, the dorsal member 12 disposed on the wearer's dorsal side, and the absorbing member 13, which is the crotch member disposed so as to bridge between these members from back to front in the crotch portion; and also, the waist opening 14, the right and left openings 15, 15, the right and left side sealing portions 16, 16, and so forth are formed As shown in FIG. 2, the ventral member 11 has a planar view in which the central portion thereof in the width direction (the waist-around direction, i.e., the X direction) of the side 11a (crotch edge) in the side (Y1 side) of the dorsal member 12 in a rectangular shape is cut out approximately in a trapezoidal shape. As shown in FIG. 2, the dorsal member 12 has a planar view that the central portion in the width direction (the waist-around direction, i.e., the X direction) of the side 12a (crotch edge) in the side (Y2 side) of the ventral member 11 in an approximately rectangular shape is projected approximately in a trapezoidal shape.

The ventral member 11 has the inner sheet 101 disposed in the inner side (skin side) and the outer sheet 102 disposed in the outer side (wearer's cloth side upon putting it on), and an elastic body 103 (103a, 103b, 103c) disposed arbitrarily between these two sheets. As shown in FIG. 1, the ventral member 11 is formed such that it may give a dent shape in its central portion in the waist-around direction, and also such that the distance (vertical length) from the leg opening 15 to the waist opening 14 may be the shortest in the neighborhood of the position where it is overlapped with the right and left edges of the absorbing member 13. Here, it is preferable that the ventral member 11 be formed such that the distance (vertical length) between the leg opening 15 and the waist opening 14 at the position where it is overlapped with the right and left edge portion of the absorbing member 13 may become 50 to 80% relative to the length (vertical length) of the side sealing portion 16. By so doing, in the pant type diaper 10, legs can be easily inserted into the leg opening 15 upon putting it on, and also the diaper can be pulled up to a hip of a wearer by holding the waist opening 14; and therefore, it can be easily put on. Moreover, even when a physically handicapped wearer such as the one having a physically paralyzed half body puts it on, by pulling up the diaper by putting a wearer's finger in the leg opening 15, the pant type diaper 10 can be pulled up to the wearer's hip, so that it can be easily put on. As shown in FIG. 2, similar to the ventral member 11, the dorsal member 12 has the inner sheet 101 disposed in the inner side (skin side) and the outer sheet 102 disposed in the outer side (cloth side), and an elastic body 103 (103a, 103b, 103d) arbitrarily disposed between these two sheets.

The inner sheet 101 and the outer sheet 102 are members having a sheet-like form made of an unwoven cloth. The inner sheet 101 and the outer sheet 102 are not limited to this; and therefore, it may be used as a resin film or a tissue, a shrinkable material or a laminate thereof, or a sheet formed by arbitrarily combining them. The elastic body 103 formed between the inner sheet 101 and the outer sheet 102 is a member having a thread-like form, and it is bonded and fixed to the inner sheet 101 and the outer sheet 102 in the extended state. The elastic body 103 like this is made of expandable materials such as a natural rubber, a polyurethane resin, and an expandable hot melt. In addition, the elastic body 103 is not limited to the thread-like form, but it may be members in the form of a belt, a sheet, or the like.

The ventral member 11 and the dorsal member 12 are formed, as discussed later, by cutting a layered body formed by laminating the inner sheet 101, the outer sheet 102, and the elastic body 103 along the cut plan line C shown in FIG. 3. The cut plan line C commonly forms the crotch edge 11a of the ventral member 11 and the crotch edge 12b of the dorsal member 12 in the X direction (the waist-around direction, i.e., the width direction), wherein from the both edges (11*b*, 11*b*, 12*b*, 12*b*) to the side of the central portions (11*d*, 12*d*) in the X direction, a pair of the tilted portions (11*c*, 11*c*, 12*c*, 12*c*) are formed slantingly toward the side of the ventral member 11, while in the X direction central portions (11*d*, 12*d*), the lines are formed in parallel to the X direction. Meanwhile, the X direction central portions (11*d*, 12*d*) of the cut plan line C may have either a curved line such as the line having a projection toward the side of the ventral side (Y2 side) or a curved line such as the line having projection toward the side of the dorsal side (Y1 side), so that it is not particularly restricted.

The width of the central portion (11*d*) of the crotch edge 11*a* of the ventral member 11 formed by the cut plan line C (this width is the size of the portion parallel to the X direction) is approximately the same as the size of the absorbing member 13 in the side of the ventral member 11 in the X direction. Also, the width of the central portion (12*d*) of the crotch edge 12*a* of the dorsal member 12 formed by the cut plan line C (this width is the size of the portion parallel to the X direction) is approximately the same as the size of the absorbing member 13 in the side of the dorsal member 12 in the X direction. Meanwhile, the width of the central portion (11*d*) of the crotch edge 11*a* of the ventral member 11 as well as the width of the central portion (12*d*) of the crotch edge 12*a* of the dorsal member 12 is not limited to these sizes, but may be narrower or broader than the width of the absorbing member 13 in the X direction.

In the Y2 side edge (waist opening 14*a*) of the ventral member 11 and the Y1 side edge of (waist opening 14*b*) of the dorsal member 12, these members making both edges of the pant type diaper 10 shown in FIG. 2 in the Y direction, between the inner sheet 101 and the outer sheet 102, the elastic body 103*a* having plural threads extended in the X direction (the waist-around direction, i.e., the width direction) are disposed in parallel and with same distance to each other in the Y direction. By so doing, the waist gather portion 17 (see FIG. 1) is formed around the waist openings 14 (14*a*, 14*b*) of the pant type diaper 10. The waist gather portion 17 provides a proper skin contact in the wearer's waist portion, so that it has functions to prevent slipping down of the pant type diaper 10 and leakage of excreta etc. from the waist opening 14 from occurring. Meanwhile, the distances in the Y direction of the elastic body 103*a* arranged therein may not be the same to each other.

In addition, in the area of the Y1 side (crotch side) of the elastic body 103*a* of the ventral member 11 and of the Y2 side (waist side) of the first leg-surrounding elastic body 103*c*, the elastic body 103*b* having plural threads extended in the X direction (the waist-around direction, i.e., the width direction) are arranged between the inner sheet 101 and the outer sheet 102 with the same distance and in parallel in the Y direction (with regard to the first leg-surrounding elastic body, explanation will be given later). Similarly, in the area of the Y2 side (crotch side) of the elastic body 103*a* of the dorsal member 12 and the Y1 side (waist side) of the second leg-surrounding elastic body 103*d*, this elastic body 103*b* is arranged between the inner sheet 101 and the outer sheet 102 (with regard to the second leg-surrounding elastic body, explanation will be given later). In so doing, the waist-around gather portion 18 is formed, so that not only the pant type diaper 10 can be contact closely with the wearer's skin but also it can function to keep the shape of the absorbing member 13; and as result, the pant type diaper 10 can fit well to the wearer's body, and the preventive effect of leakage of the excreta can be enhanced.

Meanwhile, in this embodiment, the example is shown that the distances among a plurality of the elastic body 103*b* in the Y direction are all the same; however, the distance is not limited to this, so that the distance in the Y direction arrangement may be arbitrarily adjusted in view of enhancement of fitness to around the wearer's waist, improvement in appearance, and so forth; in other word, the distances to each other may not be the same. For example, the distance of the elastic body 103*b* in the Y direction arrangement may be gradually apart as going to the crotch side of the wearer, or there may be a narrow area and a wide area in the distances of the Y direction arrangement.

As shown in FIG. 1, in the pant type diaper 10, the leg gather portions 19 are formed in the edge portions of two of the right and left leg openings 15, 15 into which the wearer's legs are inserted. The leg gather portions 19 are, for example, planar gathers, and as shown in FIG. 2, each of them is formed by arranging the first leg-surrounding elastic body 103*c* and the second leg-surrounding elastic body 103*d*, both having a plurality of thread-like form, along the crotch edge 11*a* of the ventral member 11 and the crotch edge 12*a* of the dorsal member 12. The leg gather portion 19 has a function to prevent leakage of the excreta etc. from the leg opening 15 of the pant type diaper 10 from occurring (so-called horizontal leakage). As shown in FIG. 3, the first leg-surrounding elastic body 103*c* and the second leg-surrounding elastic body 103*d*, both having the form of plural threads, expand in approximately parallel to each other along the cut pan line C, which is located between the ventral member 11 and the dorsal member 12, and are arranged in parallel in the Y direction with the same distance to each other.

As shown in FIG. 1, the side sealing portion 16 is the portion where both edges of the ventral member 11 and the dorsal member 12 in the X-direction (the waist-around direction, i.e., the width direction) are bonded. By forming the right and left side sealing portions 16, 16, the pant type is formed. The side sealing portion 16 may be formed by using an adhesive (hot melt adhesive) or the like, or by other various sealing methods such as a thermal sealing method and an ultrasonic sealing method.

Figure 4A:
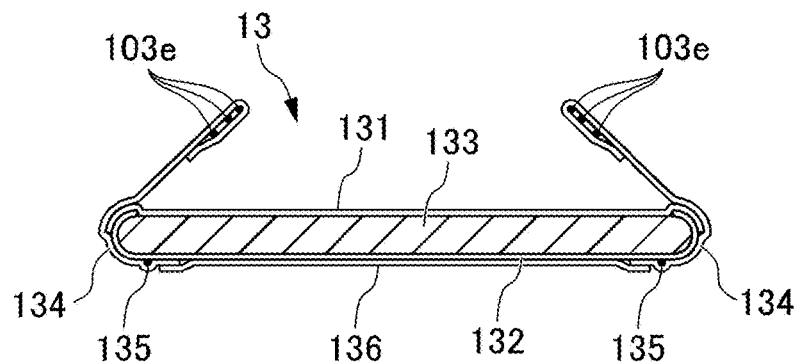
FIGS. 4A and 4B show the cross sectional views of the absorbing member 13 of the crotch member of the first embodiment cut along the line 4AB-4AB of FIG. 2.
Figure 4B:
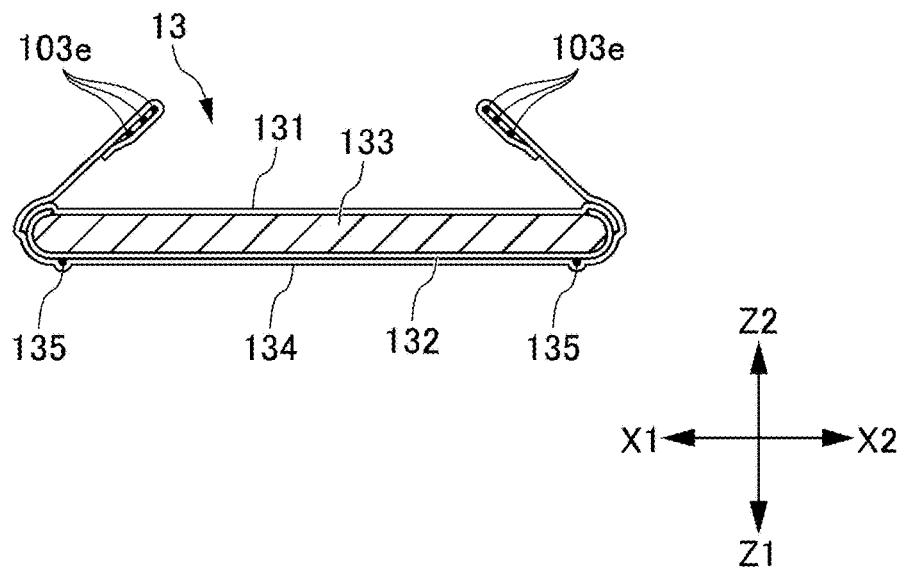

FIGS. 4A and 4B show cross sectional views of the absorbing member 13 of the crotch member according to this embodiment. FIG. 4A is the cross sectional view of an example of the absorbing member of this embodiment, and FIG. 4B is the cross sectional view of another example of this embodiment. In FIGS. 4A and 4B, the cross sectional views cut along the line 4AB-4AB in FIG. 2 are shown. The absorbing member 13 is located in the center of the ventral member 11 and the dorsal member 12 in the X direction (the waist-around direction, i.e., the width direction); and this is the crotch member which is disposed so as to bridge between the ventral member 11 and the dorsal member 12 in the Y direction (the front-back direction). The absorbing member 13 is the member having an approximately rectangular shape and comprises the front sheet 131 which is in the wearer's skin side (Z2 side), the back sheet 132 which is in the wearer's cloth side (Z1 side), the absorbing body 133 which is disposed between them, the gather sheet 134, the crotch portion elastic body 135, and the outside sheet 136. As shown in FIG. 2, the longitudinal direction of the absorbing member 13 is the Y direction (the front-back direction) and the widthwise direction is the X direction (the right and left direction, i.e., the width direction).

The front sheet 131 is formed by, for example, a member having a sheet-like form or the like which is formed by a liquid-permeable material such as an unwoven cloth; and it is arranged on the wearer's skin side upon putting it on, and has a function to permeate urine, blood, and the like to inside the absorbing member 13. The back sheet 132 is formed by, for example, a member having a sheet-like form or a film-like form which is formed by a liquid-impermeable material made of a resin such as a polyethylene film; and it is arranged on the outer side (cloth side) upon putting it on, and has a function to prevent leakage of urine, blood, and the like which are absorbed by the absorbing body 133 to outside the absorbing member 13 from occurring. The absorbing body 133 is formed by combination of absorbing materials such as an absorbing paper, a pulp having a cotton-like form, and a polymer absorbing material having absorbing property in the form of particles or fibers; and it has a function to absorb urine, blood, and the like which permeate through the front sheet 131 and keep them inside thereof. The gather sheet 134 is the sheet member to form a standing cuff in the absorbing member 13. As shown in FIG. 4A, two gather sheets 134 are formed; and each of them is bonded to the absorbing member 13 in its right edge and left edge, respectively. The gather sheet 134 is formed by, for example, an unwoven cloth or a material having an unwoven cloth adhered with a film such as a polyethylene film; and it prevents leakage of liquid bodies not absorbed by the absorbing body 133 through the crotch from occurring.

As shown in FIG. 2 and FIG. 4A, in the gather sheet 134, the elastic bodies 103e, 103e are disposed along the absorbing body 133 inside each of the folded edges in the sides of the right and left leg openings 15, 15. A plurality of the elastic body 103e are arranged in each of the gather sheet 134 (three in this embodiment), and each of them is bonded in the extended state to inside the folded portion of the gather sheet 134. By so doing, the standing cuff is formed in the position corresponding to the crotch portion of the pant type diaper 10; and thus, leakage of the liquid bodies such as excreta and urine from the crotch portion of the pant type diaper 10 can be prevented from occurring. In addition, in the gather sheet 134, the crotch portion elastic body 135 is arranged in the bonding portion with the back sheet 132.

The crotch portion elastic body 135 is the elastic member which is disposed so as to be along the right and left edges of the absorbing body 133. The crotch portion elastic body 135 is bonded between the gather sheet 134 and the back sheet 132 in the extended state. The crotch portion elastic body 135 can prevent formation of the space with the crotch from occurring even if the weight of the absorbing body is increased by absorption of the excreta to the pant type diaper 10, because the right and left edges of the absorbing member 13 are pressed to the crotch due to the tensile force of this elastic body. Besides, because the crotch portion elastic body 135 is fixed along the wearer's groin, the absorbing body 13 can contact with the wearer's crotch without twisting or loosing; and thus, extremely good fitting and leak-proof properties can be obtained.

Meanwhile, in this embodiment, the example that the crotch portion elastic body 135 is arranged as one linear line in each of the right and left edges in the width direction of the absorbing member 13 is shown; however, plural lines may be arranged in each edge, and also, curved lines may be arranged. Similarly to the elastic body 103a and the like as mentioned before, the elastic body 103e and the crotch portion elastic body 135 are made of expandable materials having a thread-like form such as a natural rubber, a polyurethane resin, and an expandable hot melt. In addition, these elastic bodies are not limited to the thread-like form, but they may be members in the form of a belt, a sheet, and the like. Besides, the entire gather portions may be formed by a material such as an expandable sheet. In this case, it is necessary to form it such that the stretching force may work in the extending direction of the elastic bodies shown in the drawings.

The outside sheet 136 is the sheet member which covers the back sheet 132 and boundary of the bonding portion of the gather sheet 134. In view of appearance and pleasant skin touch, outside of the outside sheet 136 (cloth side) may be made of the same material as the outer sheet 102 and the gather sheet 134, such as for example, an unwoven cloth. Because outside of the outside sheet 136 is located in the outermost layer below the crotch portion of the pant type diaper 10, use of the same unwoven cloth as the outer sheet 102 can provide the pant type diaper with unified appearance and skin touch. Meanwhile, in the outside sheet 136, the back sheet 132 may be served as the outermost sheet in the portion below the crotch without arranging the absorbing member 13.

The absorbing member 13 is not limited to the configuration as mentioned above; and for example, as shown in FIG. 4B, the configuration in which the gather sheet 134 covers entire outside of the back sheet 132 (opposite side of the absorbing body 133) may be employed. In this case, in the absorbing member 13, there is no need to arrange the outside sheet, so that the production cost of the absorbing member 13 may be lowered, or the process to bond the outside sheet may be omitted.

As shown in FIG. 2, the auxiliary sheet 9 is the member having a sheet-like form which covers the edge portion of the absorbing body 13 in the Y direction, whereby preventing the edge portion of the absorbing member 13 in the Y direction from touching directly to the wearer's skin. The auxiliary sheet 9 comprises members such as an unwoven cloth having a sheet-like form.

Next, the method for manufacturing the pant type diaper 10 of this embodiment will be explained. FIGS. 5A-5D show steps of manufacturing the pant type diaper 10 of the first embodiment. As shown in FIG. 5A, firstly, between the unwoven cloths having a web-like form forming the inner sheet 101 and the outer sheet 102, each elastic body 103 (103a, 103b, 103c, 103d) is arranged to form the layered body 100A having a web-like form (laminated web forming process). At this time, an adhesive or the like may be applied on surface of each elastic body 103 having a thread-like form, or an adhesive (such as a hot melt adhesive) may be applied to the bonding surface in the sides of the elastic body 103 of the inner sheet 101 and the outer sheet 102 by spray coating, or the like. Each elastic body 103 having a thread-like form is bonded with the inner sheet 101 and with the outer sheet 102 in the extended state in accordance with respective required shrinking forces. At this time, the first leg-surrounding elastic body 103c and the second leg-surrounding elastic body 103d are arranged periodically, wherein the size in the width direction (the waist-around direction) of the pant type diaper 10 in the flow direction (the X2 direction) of the layered body 100A having a web-like form is taken as one cycle.

Next, as shown in FIG. 5B, the layered body 100A having a web-like form is cut in the flow direction along the cut plan line C wherein the crotch edges 11a, 12b, which are common to the ventral member 11 and the dorsal member 12, continue periodically in the flow direction, thereby cutting this layered body into a continuous body of the ventral member 11 having the ventral members 11 continued along the flow direction in the width direction (the waist-around direction, i.e., the X direction) and a continuous body of the dorsal member 12 having the dorsal members 12 continued along the flow direction in the width direction (the waist-around direction, i.e., the X direction) (cutting process). At this time, the cut plan line C is formed periodically in the flow direction (the X direction) of the layered body 100A having a web-like form, wherein the size of the pant type diaper 10 in the width direction (the waist-around direction) is taken as one cycle. At this time, a non-cutting portion with the width of about 0.5 to 2 mm may be arbitrarily formed in part of the cut plan line C so that moving up of each member may be prevented until the members having a web-like form are separated to a prescribed distance after cutting.

Next, as shown in FIG. 5C, in the Y direction (the width direction in the layered body 100A having a web-like form, i.e., the MD direction), the ventral member 11 and the dorsal member 12 are separated with a prescribed distance in order to form the pant type. Then, by using an adhesive such as a hot melt adhesive, one edge of the absorbing member 13, i.e., the crotch member, in the longitudinal direction is bonded with the ventral member 11, and the other edge thereof is bonded with the dorsal member 12. At this time, the absorbing body 13 is bonded in such a way that the inner sheet 101 of the ventral member 11 and the dorsal member 12 may be laminated with any of the back sheet 132, the outside sheet 136, and the gather sheet 134 of the absorbing body 13 (crotch member bonding process). In this way, the continuous body 100B in that the pant type diapers in the extended state continue in the flow direction is formed.

Next, the continuous body 100B is folded such that each side of the inner sheets 101 of the ventral member 11 and of the dorsal member 12 may become the inner side; and then, the side sealing portions 16 are bonded by a heat sealing method, an ultrasonic sealing method, an adhesive (hot melting), or the like. Next, the continuous body 100B is cut along the side sealing portion 16 to form the pant type diaper 10 as shown in FIG. 5D (pant type undergarment forming process). By this cutting, the elastic bodies 103a to 103d express the shrinking force, thereby forming each of the gather portions and so forth. Meanwhile, during these processes or in processes followed thereafter, in order to facilitate removal of unwanted portions, cutting, and bonding of the crotch member, the process not to express the shrinking force in the region where the shrinking force of the elastic body is not necessary, such as the process to cut the elastic body, may be executed arbitrarily.

FIG. 6 is a drawing to explain the pant type diaper 50 of Comparative Example 1. FIG. 7 is a drawing to explain the pant type diaper 60 of Comparative Example 2. In order to help in understanding, FIG. 6 and FIG. 7 show appearances of the pant type diapers 50, 60 of Comparative Examples 1 and 2 during production process thereof. Both the pant type diapers 50, 60 of Comparative Examples 1 and 2 as shown in FIG. 6 and FIG. 7 are conventional pant type diapers. Meanwhile, with regard to the portions having the same functions as those of the pant type diaper 10 of the present embodiment as mentioned above, the same symbols are attached herein or in the last part of this specification, so that duplicated explanation will be omitted, while the absorbing body and so forth will be explained briefly.

As shown in FIG. 6, in the pant type diaper 50 of Comparative Example 1, the elastic bodies 503c, 503d are arranged around the leg openings into which the wearer's leg is inserted; and the portions to become the leg openings are excavated from the layered body 500A formed by laminating the inner sheet 101, the outer sheet 102, the elastic body 103, and so forth. And therefore, an area which is removed by excavating the layered body 500A is formed (so-called trim, shown by the area 55A in FIG. 6), resulting in a significant material loss which leads to increase in the production cost thereof.

Moreover, because the pant type diaper 50 of Comparative Example 1 as shown in FIG. 6 forms the leg openings by excavation as mentioned above, the layered body 500A having a web-like form needs to have enough size in the width direction (for example, about 70 to 100 cm for an adult user). Therefore, use amounts of the inner sheet 101 and the outer sheet 102 become so large, thereby leading to increase in the production cost thereof. In addition, under the absorbing member 13 (Z1 side), the inner sheet 101, the outer sheet 102, and the like are present. However, the inner sheet 101 and the outer sheet 102 in this part are substantially not necessary if the back sheet 132 of the absorbing member 13 has sufficient liquid-impermeability; and thus, this also leads to material loss and increase in the production cost thereof.

On the other hand, in the pant type diaper 60 of Comparative Example 2 as shown in FIG. 7, the layered body 600A laminated with the inner sheet 101, the outer sheet 102, the elastic body 103, and so forth is cut along the straight line which is parallel in the X direction (the flow direction of the layered body 600A) to form the ventral member 61 and the dorsal member 62 whereby forming rectangular forms in both the ventral member 61 and the dorsal member 62. Moreover, the elastic bodies 603c, 603d, which form the leg gather portions, are formed in parallel in the flow direction. In the pant type diaper 60 of Comparative Example 2, the absorbing member 13 is bonded with the ventral member 61 and with the dorsal member 62 with a sufficient distance between them. Accordingly, even though the size of the layered body 600A having a web-like form is smaller in the width direction than that of Comparative Example 1, the size thereof as the pant type diaper can be secured enough in the Y direction. Therefore, in the pant type diaper 60 of Comparative Example 2, the material loss and increase in the production cost, which are found in Comparative Example 1, can be suppressed.

However, in the pant type diaper 60 of Comparative Example 2, the ventral member 61 and the dorsal member 62 are both in the rectangular forms with the identical size. In general, in order to cover the hip and so forth, the dorsal member 62 requires larger area than the other member, and in addition, the shapes of the hip and the portion around the leg of a wearer are complicated; and therefore, in the pant type diaper 60 of Comparative Example 2, fitting to the wearer's body is not so good, thereby leading to easy leakage of the excreta and the like as well as unpleasant feeling upon putting it on because of twisting and so forth of the absorbing member 13, the dorsal member 62, and the like.

On the other hand, according to the pant type diaper 10 of this embodiment, as shown in FIG. 3 and FIG. 5B, the cut plan line C wherein the crotch edges 11a, 12a, which are common to the ventral member 11 and the dorsal member 12 continue periodically, has the shape of projection to the side (Y2 side) of the ventral member 11 in the width direction (the waist-around direction, i.e., the X direction) of the central portion of the pant type diaper 10, and also the first leg-surrounding elastic body 103c and the second leg-surrounding elastic body 103d, the leg gather portion 19 being formed by these two bodies, are formed along this cut plan line C; and therefore, sufficiently large area of the dorsal member 12 can be secured, and on top of it, fitting to the wearer's body can be enhanced, so that excellent use feeling can be provided.

Moreover, in the pant type diaper 10 of this embodiment, because the central portion of the ventral member 11 in the waist-around direction is in the shape of a dent, the distance from the leg opening 15 to the waist opening 14 becomes short, so that the leg can be easily inserted into the leg opening 15 upon putting it on, and also, the diaper can be pulled up to the wearer's hip by holding the waist opening 14; and thus, this can be easily put on. Furthermore, even when a physically handicapped wearer such as the one having a physically paralyzed half body puts this diaper on, by pulling up the diaper by putting the wearer's finger in the portion of the leg opening 15 where the distance to the waist opening is the shortest, the absorbing member 13 and the waist portion can be pulled up simultaneously; and thus, the pant type diaper 10 can be easily put on by pulling it up to the wearer's hip. In the pant type diaper 10 of this embodiment, the ventral member 11 and the dorsal member 12 are formed by cutting one layered body 100A having a web-like form, and the absorbing member 13 is bonded with them with a prescribed distance between these members. Accordingly, in this pant type diaper 10, even if the size in the width direction of the layered body 100A having a web-like form is made shorter than that of Comparative Example 1, sufficiently enough size as the pant type diaper 10 can be secured in the Y direction (the front-back direction). Therefore, according to the pant type diaper 10 of this embodiment, the size in the width direction of the layered body 100A having a web-like form can be made sufficiently smaller as compared with Comparative Example 1 (for example, about half of the layered body 500A of Comparative Example 1), and there is no area to be excavated as the leg opening; and thus, the material loss and increase in the production cost as mentioned before can be suppressed.

According to the pant type diaper 10 of this embodiment, as shown in FIG. 1, in the crotch edge 11a in the ventral side, the right and left leg openings 15, 15 are tilted (11c), downward (toward the wearer's leg) from the crotch side (11d) to the side thereof (11b), and in the crotch edge 12a in the dorsal side, they are tilted (12c) downward (toward the wearer's leg) from the side thereof (12b) to the crotch side (12d); and thus, it can be fit well without squeezing around the wearer's leg. In addition, because the front opening is wide, upon putting it on, the leg can be easily inserted into the leg opening 15 without the wearer's tiptoes being caught.

As discussed above, according to this embodiment, the pant type diaper 10, i.e., the disposable pant type undergarment which can be easily put on even by a physically handicapped wearer, and which can fit well to the wearer's body thereby giving an excellent wear feeling, and further which can be produced by using small amount of the materials thereby reducing the production cost thereof, can be provided.

Second Embodiment

Figure 8:
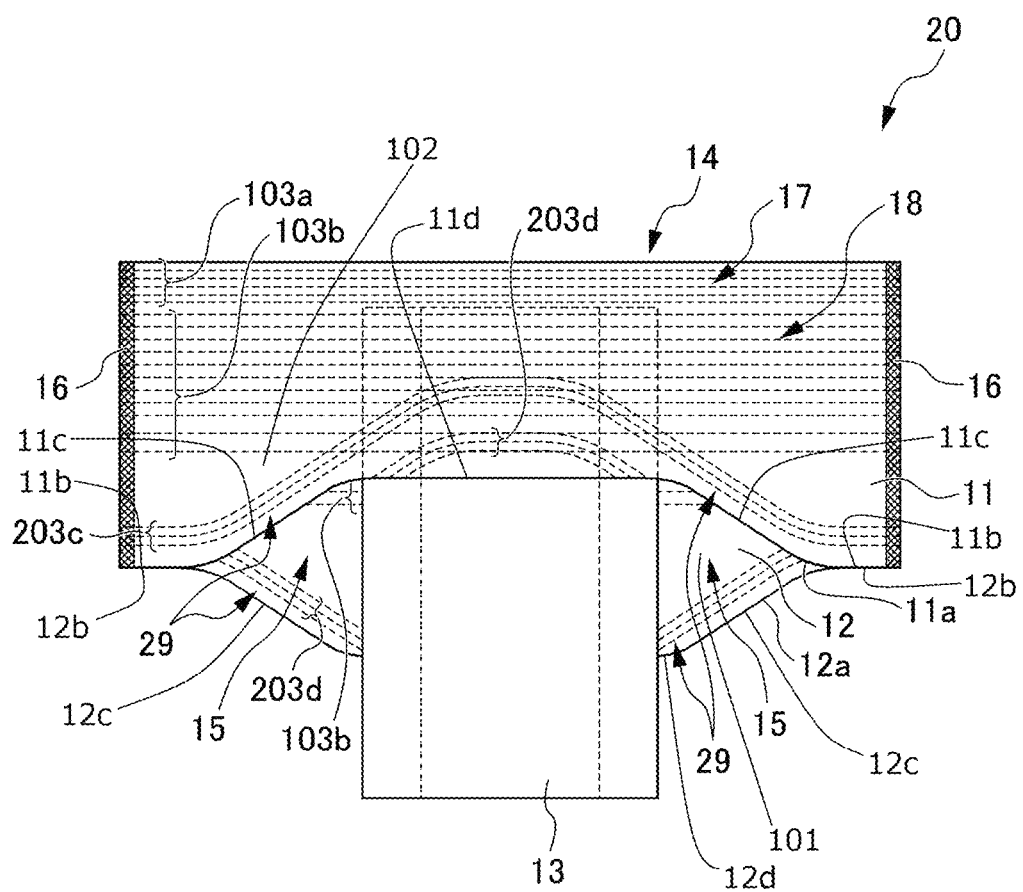
FIG. 8 is a drawing to explain the pant type diaper 20 of a second embodiment.
Figure 9:
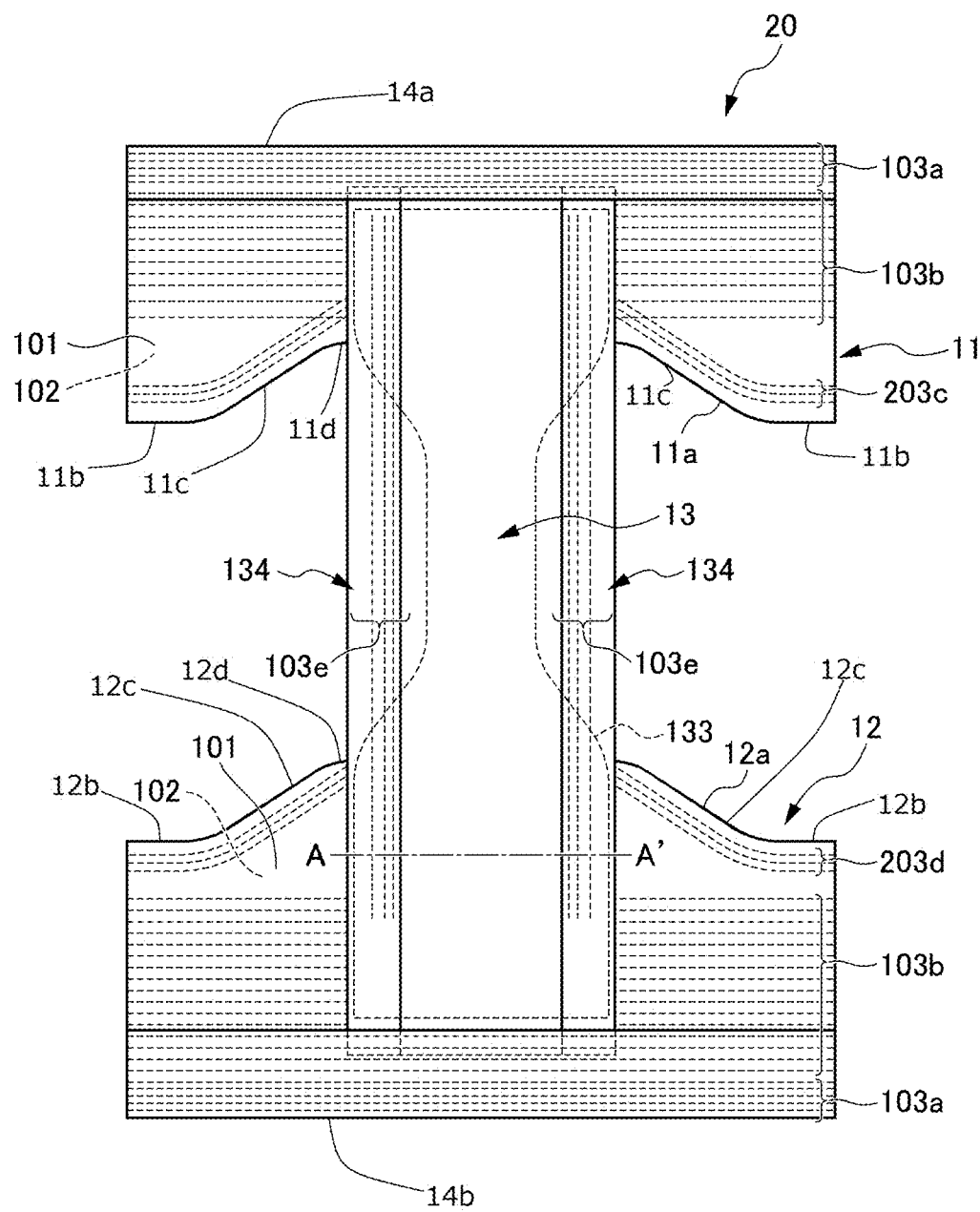
FIG. 9 is a drawing to show the pant type diaper 20 of the second embodiment that is extended to a planar view.
Figure 10:
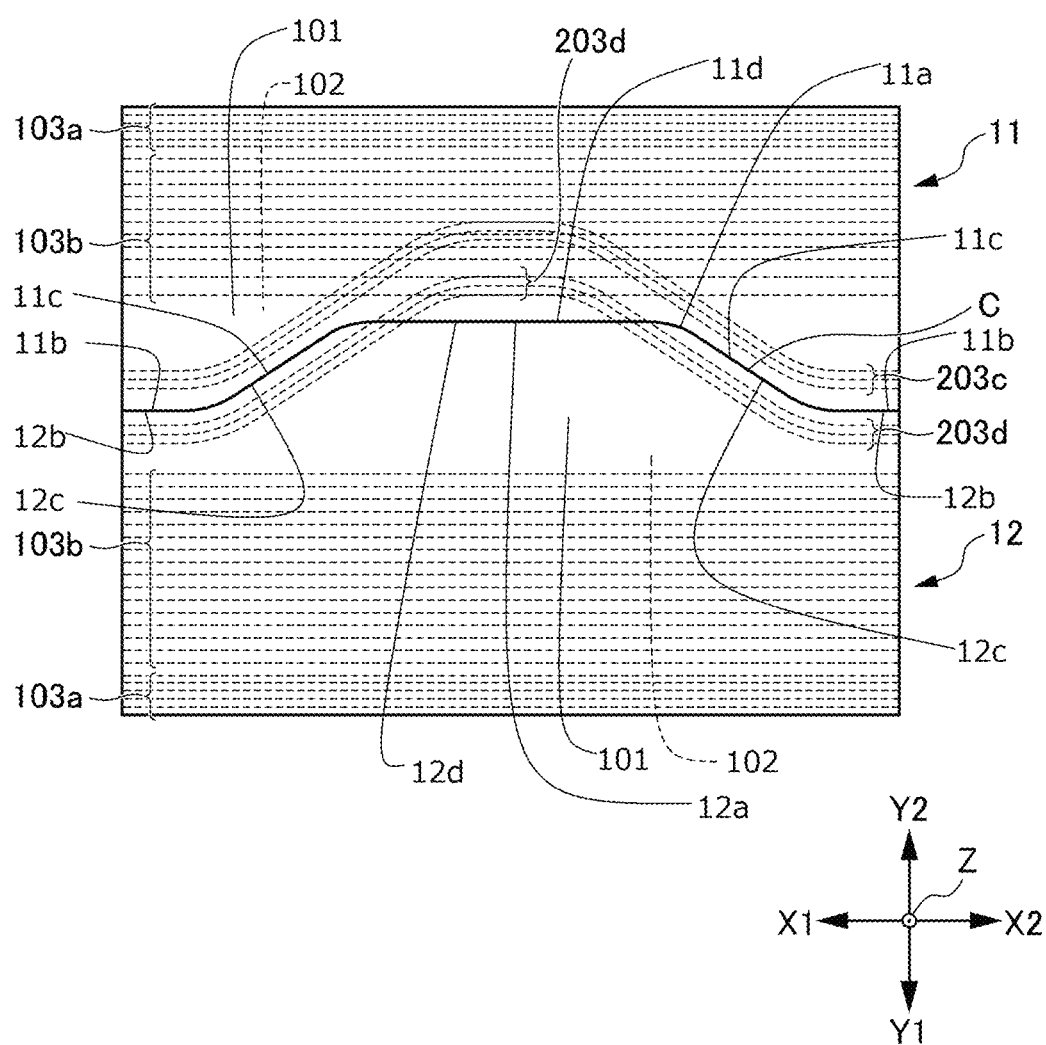
FIG. 10 is a drawing to explain the first leg-surrounding elastic body 203c, the second leg-surrounding elastic body 203d, and the cut plan line C of the pant type diaper 20 of the second embodiment.

FIG. 8 is a drawing to show the pant type diaper 20 of the second embodiment. FIG. 9 is a drawing to show the pant type diaper 20 of the second embodiment that is extended to a planar view. FIG. 10 is a drawing to explain the first leg-surrounding elastic body 203c, the second leg-surrounding elastic body 203d, and the cut plan line C of the pant type diaper 20 of the second embodiment.

The pant type diaper 20, which is the second embodiment of the disposable pant type undergarment of the present invention, has the same form as that of the pant type diaper 10 of the first embodiment mentioned above, except that the forms of the first leg-surrounding elastic body 203c and the second leg-surrounding elastic body 203d, both having plural threads and forming the leg gather portion 29, are different from those of the above-mentioned first embodiment. Therefore, with regard to the portions having the same functions as those of the first embodiment as mentioned above, the same symbols are attached herein or in the last part of this specification, so that duplicated explanation will be arbitrarily omitted. The pant type diaper 20 of the second embodiment comprises the ventral member 11, the dorsal member 12, and the absorbing member 13 which is the crotch member; and also, the waist opening 14, the right and left leg openings 15, 15, the right and left side sealing portions 16, 16, and so forth are formed. In addition, in this pant type diaper 20, the waist gather portion 17, the waist-around gather portion 18, the leg gather portion 29, and so forth are formed.

In this pant type diaper 20, as shown in FIG. 8 to FIG. 10, the first leg-surrounding elastic body 203c and the second leg-surrounding elastic body 203d, both having plural threads and forming the leg gather portion 29, are extended approximately parallel to each other; and in both edge portions thereof in the X direction (the waist-around direction, i.e., the width direction), they are disposed in parallel with having the cut plan line C between them, but it has the form that the central portion thereof is inside (Y2 side) of the ventral member 11 beyond the cut plan line C. That is, part of the second leg-surrounding elastic body 203d arranged in the side of the dorsal member 12 is inside the ventral member 11 beyond the cut plan line C. Accordingly, in the cutting process, the second leg-surrounding elastic body 203d is cut to give the form that portion thereof is left in the central portion in the width direction of the ventral member 11. Meanwhile, the cut plan line C of this embodiment is the same as the cut plan line C of the before-mentioned first embodiment.

By arranging the first leg-surrounding elastic body 203c and the second leg-surrounding elastic body 203d in the form like this, in the pant type diaper 20 of the second embodiment, as shown in FIG. 8 to FIG. 10, in both the ventral member 11 and the dorsal member 12, the lengths of the portions where the first leg-surrounding elastic body 203c and the second leg-surrounding elastic body 203d are extended slantingly upward (toward the waist side of the wearer), these bodies being arranged in the edges of the right and left leg openings 15, 15, are longer than those of the pant type diaper 10 (see FIG. 3) of the first embodiment. Meanwhile, the pant type diaper 20 of this embodiment can be produced by the approximately same production method as that of the pant type diaper 10 of the before-mentioned first embodiment, except that the arrangement forms of the first leg-surrounding elastic body 203c and the second leg-surrounding elastic body 203d are different.

By arranging the first leg-surrounding elastic body 203c and the second leg-surrounding elastic body 203d in the form as mentioned above, the lengths of the portions where the first leg-surrounding elastic body 203c and the second leg-surrounding elastic body 203d are extended slantingly upward (toward the waist side of the wearer), these bodies being arranged in the edges of the right and left leg openings 15, 15, become longer, so that in the ventral side, the effect of pulling up of the both side portions of the ventral portion to the central portion thereof by pulling up the central portion of the ventral portion is high. Therefore, when the wearer inserts the leg thereof into the leg opening 15, entire of the pant type diaper 20 can be easily pulled up by pulling up the central portion of the ventral side only by one hand. Therefore, according to the pant type diaper 20 of this embodiment, for example, even a wearer having a physically paralyzed half body or the like can easily put on the pant type diaper 20 by oneself. In addition, according to this embodiment, because part of the second leg-surrounding elastic body 203d is arranged slantingly upward (the wearer's waist side) in the neighborhood of the central portion of the ventral member 11 in the width direction, it can function as the elastic body to form the leg gather portion; and thus, the contact with around the wearer's leg is improved, so that leakage of urine and so forth can be prevented from occurring. Meanwhile, with regard to the second leg-surrounding elastic body 203d which is extended in parallel in the X direction in the central portion of the ventral member 11 in the width direction, in view of suppressing wrinkles formed in the absorbing member 13, improving appearance and skin touch to the ventral, and the like, the process such as cutting this elastic body into pieces may be executed so as not to exert the shrinking force thereof. In addition, according to this embodiment, similarly to the before-mentioned first embodiment, the pant type diaper 20, i.e., a disposable pant type undergarment which can be easily put on even by a physically handicapped wearer, and which fits well to the wearer's body with giving an excellent wear feeling, and which can be produced with small amount of the materials and with a low production cost can be provided.

Third Embodiment

Figure 11:
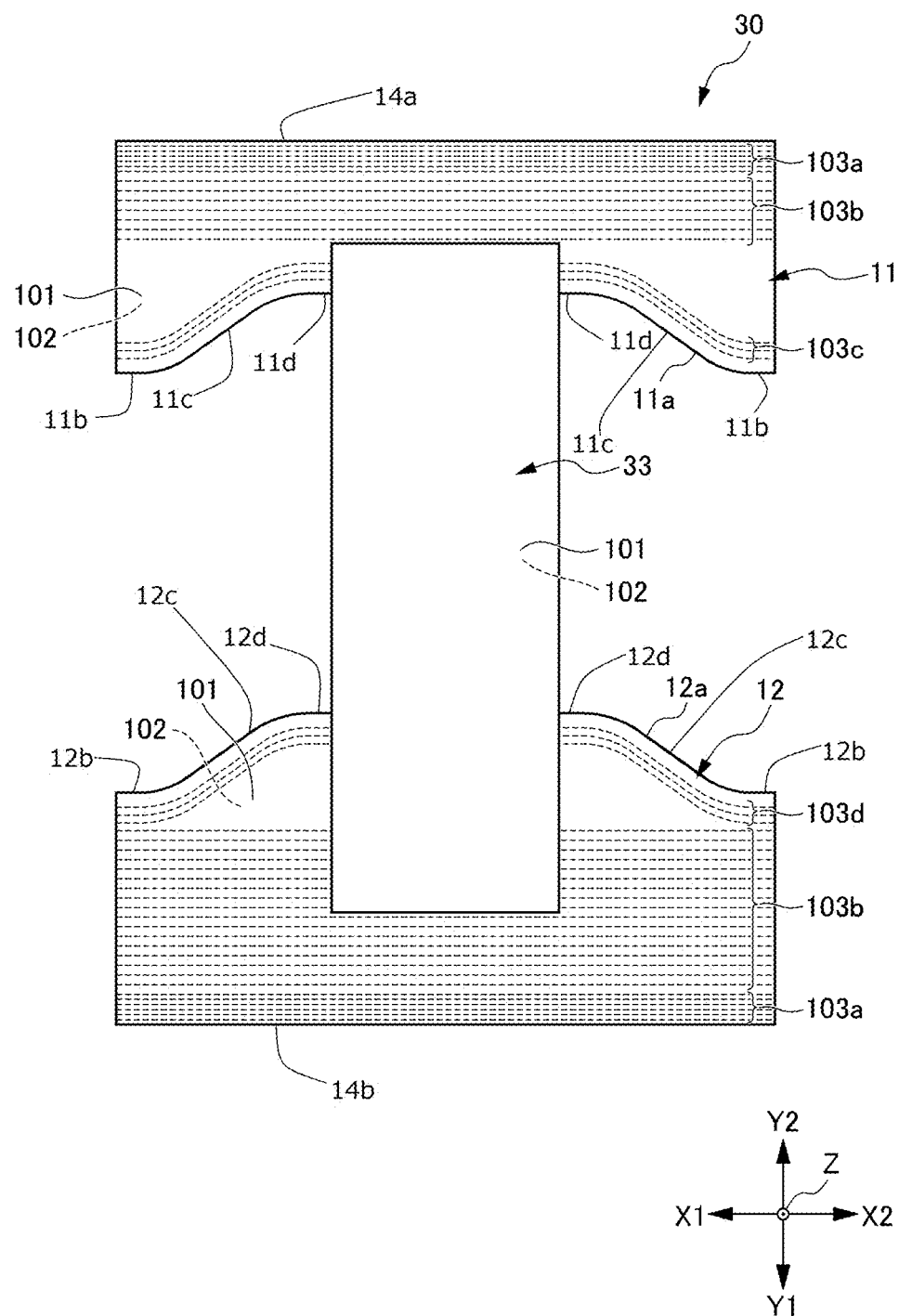
FIG. 11 shows the pant type pad holder 30 of a third embodiment that is extended to a planar view.

FIG. 11 is a drawing to show the pant type pad holder 30 of the third embodiment that is extended to a planar view. The pant type pad holder 30 which is the third embodiment of the disposable pant type undergarment of the present invention has approximately the same form as the pant type diaper 10 of the first embodiment except that it is different from the before-mentioned first embodiment in that it is provided with the crotch member 33 in place of the absorbing member 13. Therefore, with regard to the portions having the same functions as those of the first embodiment as mentioned above, the same symbols are attached herein or in the last part of this specification, so that duplicated explanation will be arbitrarily omitted. The pant type pad holder 30 of this embodiment comprises the ventral member 11, the dorsal member 12, and the crotch member 33, and also has the waist gather portion formed in the wearer's waist portion, and others. This pant type pad holder 30 may be provided with a general absorbing substance (so-called pad) in the rectangular shape or the like on the crotch member 33 (skin side), and therefore, this is a disposable pant type undergarment which is used by putting the absorbing substance on the crotch member 33.

The crotch member 33 is formed, similarly to the ventral member 11 and so forth, by laminating the inner sheet 101 and the outer sheet 102. Meanwhile, the crotch member 33 is not limited to this, but similarly to the before-mentioned absorbing member 13, it may be in the form that the front sheet 131 is laminated with the back sheet 132. Alternatively, the crotch member 33 may be in the form that there is, such as for example, an absorbing body (not shown by the drawing) having a weaker absorption ability than the absorbing body 133 of the absorbing member 13 between the inner sheet 101 and the outer sheet 102 (or between the front sheet 131 and the back sheet 132). Still alternatively, in the crotch member 33, a standing cuff portion, a planar gather portion, or the like may be formed in both edge portions of the widthwise direction thereof (the X direction, i.e., the waist-around direction) by plural elastic bodies and so forth having a thread-like form which are arranged in the extended state in the longitudinal direction (the Y direction). Meanwhile, this pant type pad holder 30 may be produced by approximately the same production method as that of the pant type diaper 10 of the before-mentioned first embodiment except that the absorbing member 13 is changed to the crotch member 33.

According to this embodiment, the pant type pad holder 30, i.e., a disposable pant type undergarment which can be easily put on even by a physically handicapped wearer, and which can fit well to the wearer's body thereby giving an excellent wear feeling, and further which can be produced by using small amount of the materials thereby reducing the production cost thereof can be provided. Meanwhile, in this pant type pad holder 30, the absorbing member 13 of the pant type diaper 20 of the second embodiment may be used as the crotch member 33 as well. This form of the pant type pad holder 30 can reduce the production cost and improve the fitness to the body; and on top of it, the wearer can easily insert the leg thereof into the leg opening 15, and also, the wearer can easily pull up the pant type pad holder 30 even with one hand.

Fourth Embodiment

Figure 12:
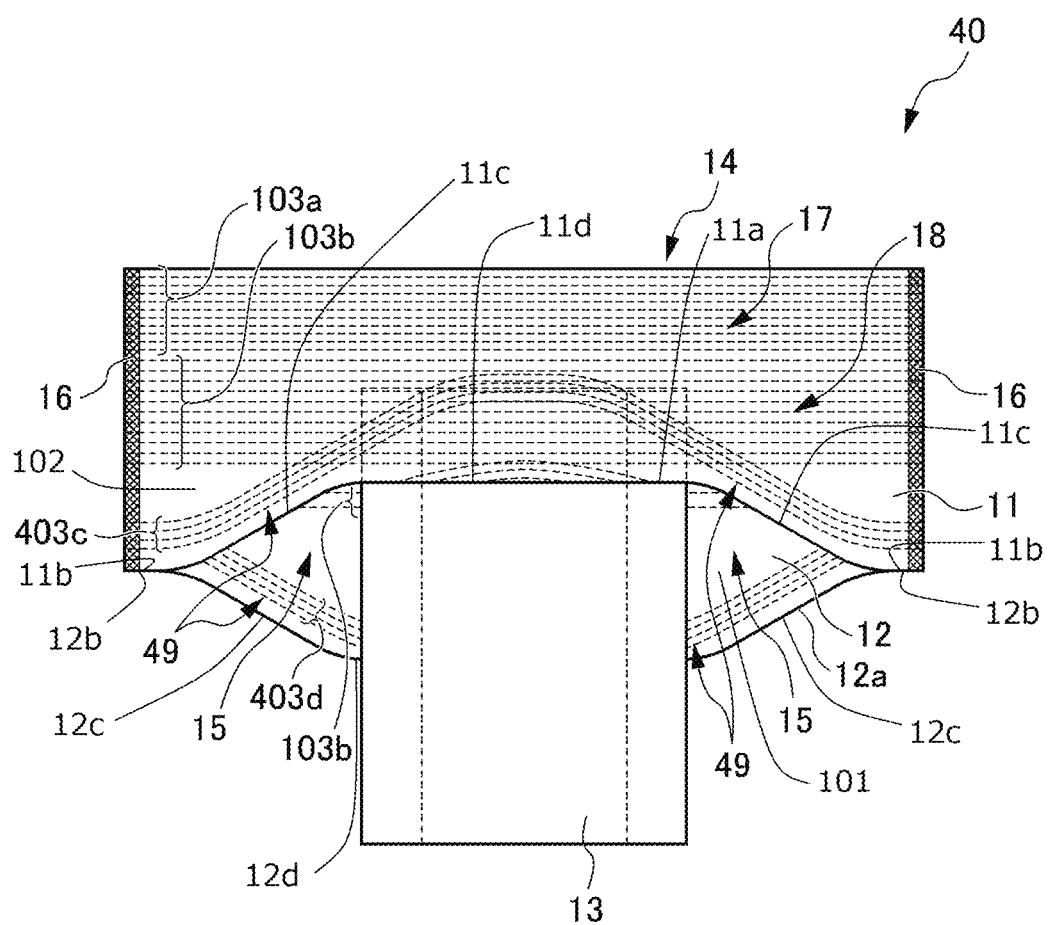
FIG. 12 shows the pant type diaper 40 of the fourth embodiment.
Figure 13:
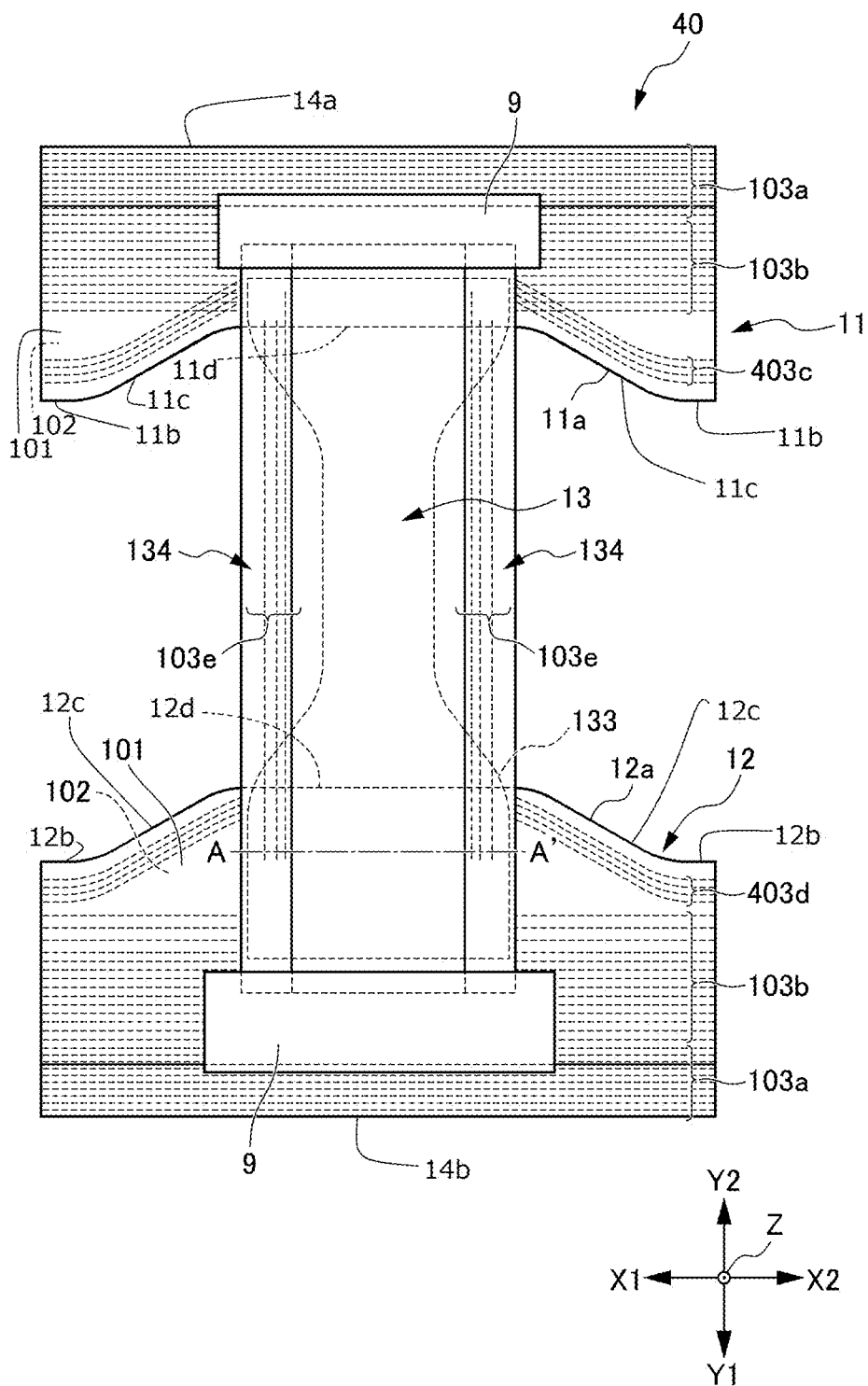
FIG. 13 shows the pant type diaper 40 of a fourth embodiment that is extended to a planar view.
Figure 14:
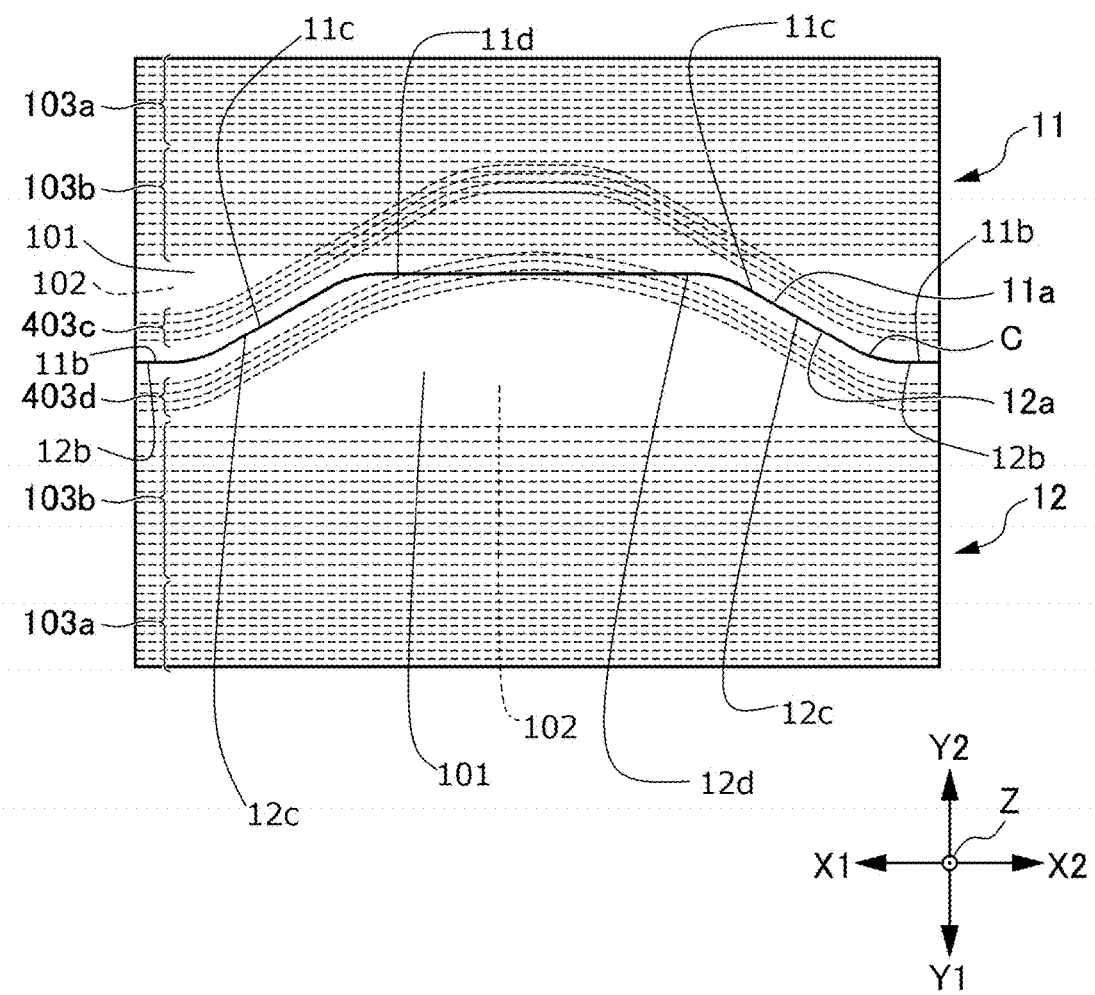
FIG. 14 shows the first leg-surrounding elastic body 403c, the second leg-surrounding elastic body 403d, and the cut plan line C of the pant type diaper 40 of the fourth embodiment.

FIG. 12 is a drawing to show the pant type diaper 40 of the fourth embodiment. FIG. 13 is a drawing to show the pant type diaper 40 of the fourth embodiment that is extended to a planar view. FIG. 14 is a drawing to explain the first leg-surrounding elastic body 403c, the second leg-surrounding elastic body 403d, and the cut plan line C of the pant type diaper 40 of the fourth embodiment.

The pant type diaper 40, which is the fourth embodiment of the disposable pant type undergarment of the present invention, has the same form as that of the pant type diaper 10 of the first embodiment mentioned above, except that the forms of the first leg-surrounding elastic body 403c and the second leg-surrounding elastic body 403d, both of which have plural threads and form the leg gather portion 49, are different from those of the above-mentioned first embodiment, and that part of the second leg-surrounding elastic body 403d having a thread-like form is not cut. Therefore, with regard to the portions having the same functions as those of the first embodiment as mentioned above, the same symbols are attached herein or in the last part of this specification, so that duplicated explanation will be arbitrarily omitted. The pant type diaper 40 of the fourth embodiment comprises the ventral member 11, the dorsal member 12, and the absorbing member 13, which is the crotch member; and also, the waist opening 14, the right and left leg openings 15, 15, the right and left side sealing portions 16, 16, and so forth are formed therein. In addition, in this pant type diaper 40, the waist gather portion 17, the waist-around gather portion 18, the leg gather portion 49, and so forth are formed.

In this pant type diaper 40, as shown in FIG. 12, the first leg-surrounding elastic body 403c and the second leg-surrounding elastic body 403d, both of which have plural threads and form the leg gather portion 49, are extended approximately parallel to each other in the X direction (the waist-around direction, i.e., the width direction) in both edge portions thereof; however, in the X direction (the waist-around direction, i.e., the width direction) in the central portion thereof, they are not parallel, wherein the second leg-surrounding elastic body 403d is arranged in the shape of a curved line to form a projection toward the side of the ventral member 11 (toward the side of the waist opening 14). In addition, as shown in FIG. 14, the second leg-surrounding elastic body 403d has the shape that in the X direction (the waist-around direction, i.e., the width direction) in central portion, part of the elastic body having plural threads arranged in the Y direction is in the side of the ventral member 11 (the Y2 side) beyond the cut plan line C, and portion thereof is in the side of the dorsal member 12 (the Y1 side). Namely, in the second leg-surrounding elastic body 403d, in the cutting process, portion thereof is in the side of the ventral member 11 by cutting, while portion thereof is not cut so that it is in the side of the dorsal member 12. The cut plan line C of this embodiment is the same as the cut plan line C of the before-mentioned first embodiment.

In the pant type diaper 40, as shown in FIG. 13 and so forth, in the ventral member 11, the elastic body 103b, which is located in the area between the cut plan line C and the first leg-surrounding elastic body 403c, and the second leg-surrounding elastic body 403d, and, in the dorsal member 12, the second leg-surrounding elastic body 403d which is located in the central portion in the X direction (the waist-around direction) are processed such that they do not express their shrinking forces. Here, the second leg-surrounding elastic body 403d which is located in the dorsal member 12 is processed such that it does not express its shrinking force in the area where it is overlapped with the absorbing member 13, which is the crotch member, except for the area around both the right and left edges of the absorbing member 13.

The measures as mentioned above are made in order to suppress wrinkles formed in the absorbing member 13 as well as to improve the appearance, the skin touch to the wearer's ventral, and the like. Meanwhile, as to the process not to express the shrinking force of the elastic bodies, for example, cutting of the elastic bodies by many projections, a cutter knife, or the like, and a thermal sealing method, and so force may be arbitrarily selected for use. The pant type diaper 40 of this embodiment may be produced by approximately the same production method as that of the pant type diaper 10 of the before-mentioned first embodiment except that the form and the like to arrange the first leg-surrounding elastic body 403c and the second leg-surrounding elastic body 403d are different.

In the pant type diaper 40 of the fourth embodiment, by arranging the first leg-surrounding elastic body 403c and the second leg-surrounding elastic body 403d in the form as mentioned above, as shown in FIG. 12 to FIG. 14, in both the ventral member 11 and the dorsal member 12, the lengths of the portions extended slantingly upward (toward the waist side of the wearer) in the first leg-surrounding elastic body 403c and the second leg-surrounding elastic body 403d, which are arranged in the edges of the right and left leg openings 15, 15, become longer than the lengths of the pant type diaper 10 of the first embodiment (see FIG. 3). Accordingly, because of the first leg-surrounding elastic body 403c and the second leg-surrounding elastic body 403d, in the ventral side, the effect of pulling up of the both side portions to the central portion of the ventral by pulling up the central portion of the ventral portion is high. Therefore, when the wearer inserts the leg thereof into the leg opening 15, entire of the pant type diaper 40 can be easily pulled up by pulling up the central portion of the ventral side only by one hand. Therefore, according to this embodiment, even the wearer having a physically paralyzed half body or the like can easily put on the pant type diaper 40 by oneself.

Moreover, according to this embodiment, because the second leg-surrounding elastic body 403d other than the portion near the right and left edges of the absorbing member 13 in the area where the dorsal member 12 and the absorbing member 13 are overlapped is located in the side of the dorsal member 12 in the state of not expressing the shrinking force by cutting or the like, when the ventral member 11 and the dorsal member 12 are cut by the cut plan line C, it is possible to suppress curling or wrinkling due to the shrinking force of the second leg-surrounding elastic body 403d in the bonding portion of the dorsal member 12 with the absorbing member 13 (the portion with the shape of projection in the dorsal member 12). In addition, according to this embodiment, similarly to the before-mentioned first embodiment, the pant type diaper 40, i.e., a disposable pant type undergarment which can be easily put on even by a physically handicapped wearer, and which fits well to the wearer's body with giving an excellent wear feeling, and which can be produced with small amount of the materials, and which can be produced with the lowered production cost can be provided.

Modified Embodiment

Not limited to the embodiments explained above, various modifications and changes thereof are possible; and these are also within the scope of the present invention.

In the inner sheet 101, the outer sheet 102, the front sheet 131, the back sheet 132, the absorbing body 133, and so forth, materials and forms other than those mentioned above may be used as well.

The pant type diapers 10, 20 and the pant type pad holder 30 are not necessarily provided with the leakage-protection mechanism such as the standing cuff portion, the planar gather portion, the waist gather portion, and the like; they may not be provided with some of them or all of them, or they may be provided with a leakage-protection mechanism other than those mentioned above.

The absorbing member 13 and the crotch member 33 having the rectangular shape have been shown as examples; however, the shape thereof is not limited to this, so that other shape may be used as well.

FIG. 15 is a drawing to explain the shape of the absorbing member 13 (crotch member 33), which is the modified embodiment. FIG. 15A is the pant type diaper extended to a planar view, and FIG. 15B is the pant type diaper viewed from the ventral side. Meanwhile, in FIG. 15, in order to help in understanding, the elastic bodies and so forth are omitted.

For example, as shown in FIG. 15, it may be the form that both edges in the widthwise direction (the right and left direction, i.e., the width direction and the X direction) are cut out in a curved line or the like in accordance with the wearer's crotch width, and the like. Alternatively, it may be a shape of a so-called hour glass wherein width in the central portion in the longitudinal direction is made narrow. In this example, after the absorbing member 13 (the crotch member 33) is cut out in a curved line or in the shape of an hour glass, it may be bonded with the ventral member and with the dorsal member; or alternatively, after the rectangular absorbing member is bonded with the ventral member and with the dorsal member, an unnecessary portions thereof may be cut out in a curved line or in the shape of an hour glass. In the case that after the absorbing member having the rectangular shape is bonded with the ventral member and with the dorsal member an unnecessary portions thereof are removed by cutting, a cutting out process to form the leg openings may be arranged, wherein in this process both edge portions in the waist-around direction (the widthwise direction, i.e., the X direction) of the absorbing member are cut out in a curved line, and also part of the ventral member and part of the dorsal member are cut out such that curved lines thereof may be drawn so as to be continuous with the curved lines of the cut-out absorbing member. By simultaneously cutting out the absorbing member as well as the ventral member and the dorsal member in the way as mentioned above, a curved line having better appearance as the undergarment can be realized; and moreover, not only the fitness to the wearer's body can be improved but also the material loss that is wasted by cutting out can be suppressed to a minimum. Besides, by arbitrarily forming a standing cuff portion or a planar gather portion, the function to prevent leakage of urine and so forth may be improved. Meanwhile, the form of the absorbing body arranged in the absorbing member 13 and the like may be arbitrarily changed.

Meanwhile, although each embodiment and modified embodiment may be arbitrarily combined for use, the detailed explanation thereof is omitted. Besides, the present invention is not restricted by each embodiment and so forth explained above.

What is claimed is:

1. A disposable pant type undergarment, comprising:
    a ventral member;
    a dorsal member;
    a crotch member that bridges the ventral member and the dorsal member bonded at center portions of the ventral member and the dorsal member;
    a waist opening surrounded by the ventral member and the dorsal member, wherein right and left side edges of the ventral member and right and left side edges of the dorsal member being bonded;
    right and left leg openings surrounded by the ventral member, the dorsal member and the crotch member;
    waist elastic bodies extended on the ventral member and the dorsal member in a waist-around direction;
    a first leg-surrounding elastic body extended at least on the ventral member around the right and left leg openings; and
    a second leg-surrounding elastic body extended at least on the dorsal member around the right and left leg openings; wherein
    a crotch edge of the ventral member comprises right and left edge lines, right and left tilted lines and a central line, the edge lines are approximately parallel in the waist-around direction, the edge lines are connected to the tilted lines, the tilted lines are connected to the central line, a first distance extending between the tilted lines and the waist opening at a position adjacent the central line; wherein
    a crotch edge of the dorsal member comprises right and left edge lines, right and left tilted lines and a central line, the edge lines are approximately parallel in the waist-around direction, the edge lines are connected to the tilted lines, the tilted lines are connected to the central line, a second distance extending between the tilted lines and the waist opening at a position adjacent the central line, the second distance being greater than the first distance; wherein
    the first leg-surrounding elastic body comprises right and left edge portions, right and left tilted portions and a central portion, the edge portions are extended along the edge lines of the ventral member, the edge portions are connected to the tilted portions, the tilted portions are connected to the central portion, the tilted portions extend in a leaving direction from the crotch edge of the ventral member such that a distance between the tilted portions and the crotch edge increases as the tilted portions approach a center of the crotch member, the tilted portions extending into an area overlapped with the ventral member and the crotch member; and wherein
    the second leg-surrounding elastic body comprises right and left edge portions, right and left tilted portions and a central portion, the edge portions are extended along the edge lines of the dorsal member, the edge portions are connected to the tilted portions, the tilted portions are connected to the central portion, the tilted portions extend in an approaching direction to the crotch edge of the dorsal member such that a distance between the tilted portions and the crotch edge decreases as the tilted portions approach a center of the crotch member.

2. The disposable pant type undergarment according to claim 1, wherein the right and left tilted portions of the first leg-surrounding elastic body cross the waist elastic bodies extended on the ventral member in the waist-around direction.

3. The disposable pant type undergarment according to claim 1, wherein the right and left tilted portions of the second leg-surrounding elastic body cross the crotch edge of the dorsal member.

4. The disposable pant type undergarment according to claim 1, wherein an absorbing body is attached to an inside or an outside the crotch member; and wherein the waist elastic bodies or the first or second leg-surrounding elastic body have a portion that is extinguished elasticity and disposed at an area overlapped with the absorbing body and the ventral member or the dorsal member.

5. A method for manufacturing the disposable pant type undergarment according to claim 1, the method comprising:
    forming a web-like layered body, wherein the layered body comprises an inner sheet and an outer sheet, the layered body further comprises the waist elastic bodies, the first leg-surrounding elastic body and the second leg-surrounding elastic body between the inner sheet and the outer sheet, the waist elastic bodies are extended in a web stream direction, the first elastic body and the second elastic body are extended periodically in a web stream direction;
    cutting the layered body along a cut plan line thereby dividing the layered body into a first continuous body that comprises the ventral member and a second continuous body that comprises the dorsal member, wherein the cut plan line includes the crotch edge of the ventral member that coincides the crotch edge of the dorsal member, the first leg-surrounding elastic body and the second leg-surrounding elastic body are arranged along the cut plan line;
    widening the distance between the first and second continuous bodies in a web-width direction;
    bonding the crotch member onto the ventral member and the dorsal member at the central portions of the ventral member and the dorsal member;
    folding the first and second continuous bodies at the crotch member so that the inner sheets of the first and second continuous bodies meet together;
    bonding the continuous bodies at a line perpendicular to the web stream direction in every periodicity; and
    cutting the bonded continuous bodies in every periodicity to form the pant type undergarments.

6. The method for manufacturing the disposable pant type undergarment according to claim 5,
    wherein the step of forming the web-like layered body comprising the step of: disposing part of the tilted portions of the second leg-surrounding elastic body at the area that the crotch member and the ventral member overlap by crossing the cut plan line; and wherein the step of cutting the layered body along the cut plan line comprising the step of: cutting the second leg-surrounding elastic body at the cut plan line.

\* \* \* \* \*